US005574205A

United States Patent [19]
Kucherlapati et al.

[11] Patent Number: 5,574,205
[45] Date of Patent: Nov. 12, 1996

[54] HOMOLOGOUS RECOMBINATION FOR UNIVERSAL DONOR CELLS AND CHIMERIC MAMMALIAN HOSTS

[75] Inventors: Raju Kucherlapati, Darien, Conn.; Beverly H. Koller, Carrboro; Oliver Smithies, Chapel Hill, both of N.C.; Robert B. Dubridge, Belmont, Calif.; Gary Greenburg, San Carlos, Calif.; Daniel J. Capon, Hillsborough, Calif.; Steven R. Williams, San Francisco, Calif.; Mariona L. A. De Rafael, Barcelona, Spain

[73] Assignee: Cell Genesys, Foster City, Calif.

[21] Appl. No.: 175,469

[22] Filed: Dec. 30, 1993

Related U.S. Application Data

[63] Continuation-in-part of Ser. No. 990,879, Dec. 19, 1992, Pat. No. 5,413,923, which is a continuation-in-part of Ser. No. 611,020, filed as PCT/US90/04178, Jul. 25, 1990, Pat. No. 5,416,260, which is a continuation-in-part of Ser. No. 431,872, Nov. 19, 1989, abandoned, and Ser. No. 385,651, Jul. 19, 1989, abandoned.

[51] Int. Cl.$^6$ .............................. C12N 15/00; C12N 5/00; A61K 48/00; A61K 49/00
[52] U.S. Cl. ............................ 800/2; 424/9.2; 424/93.21; 435/172.3; 435/320.1; 435/240.2; 800/DIG. 1; 800/DIG. 2; 935/62; 935/111
[58] Field of Search .................................. 800/2, DIG. 1, 800/DIG. 2; 435/172.3, 320.1, 317.1; 424/9.2, 93.21; 935/62, 111

[56] References Cited

PUBLICATIONS

Aguet et al., Cell 55:273–280 (1988).
Koller et al., Science 248:1227–1230 (1990).
Kucherlapati et al. (1984) P.N.A.S. USA 81:3153–3157.
Kucherlapati et al. (1985) Mol. and Cell. Biol. 5: 714–720.
Smithies et al. (1985) Nature 317: 230–234.
Wake et al. (1985) Mol. and Cell. Biol. 8:2080–2089.
Ayares et al. (1985) Genetics 111: 375–388.
Ayares et al. (1986) Mol. and Cell. Bio. 7:1656–1662.
Song et al. (1987) P.N.A.S. USA 84:6220–6824.
Thomas and Capecchi (1987) Cell 51:503–512.
Nandi et al. (1988) P.N.A.S. USA 85:3845–3849.
Mansour et al. (1988) Nature 336: 348–352.
Evans and Kaufman (1981) Nature 294:146–154.
Doetschman et al. (1987) Nature 330:576–578.
Thomas et al. (1989) Cell 56:316–321.
Kim and Smithies (1988) Nucleic Acids Res. 16:8887–8903.
Joyner et al. (1989) Nature 338:153–156.
Linney and Donnerly (1983) Cell 35:693–699.
Sullivan et al. (1985) J. Clin Invest. 76:75–79.
Lisowska–Grospierre et al. (1985) J. Clin. Invest 76:381–385.
Arens et al. (1987) J. Inf. Dis. 156:837–841.
Clement et al. (1988) J. Clin. Invest. 81:669–675.
Sugiyama et al. (1986) Chest 89:398–401.
Hume et al. (1989) Human Immunology 25:1–11.
Germain et al. (1993) Ann. Rev. Immunol. 11:403–450.
Pestka et al. (1987) Ann. Rev. Biochem. 56:727–777.
Rosa et al. (1984) Immunol. Today 5:262–262.
Trowsdale et al. (1990) Nature 348:741–744.
Schwartzberg et al. (1990) P.N.A.S. USA 87:3210–3214.
Jasin et al. (1990) Genes & Development 4:157–166.
Doetschman et al. (1988) P.N.A.S. USA 85:8583–8587.
Sedivy and Sharp (1989) P.N.A.S. USA 86:227–231.
Riele et al. (1990) Letters to Nature 348:649–651.
Jeannotte et al. (1991) Mol. and Cell. Biol. 11(11):5578–5585.
Charron et al. (1990) Mol. and Cell. Biol. 10(4):1799–1804.
Stanton et al. (1990) Mol. and Cell Bio. 10(12):6755–6758.
Mortensen et al. (1992) Mol. and Cell. Biol. 12(5):2391–2395.
Patel et al. (1986) Mol. and Cell Biol. 6(2):393–403.
Maddon et al. (1985) Cell 42:93–104.

Primary Examiner—Jasemine C. Chambers
Attorney, Agent, or Firm—Cell Genesys

[57] ABSTRACT

Homologous recombination is employed to inactivate genes, particularly genes associated with MHC antigens. Particularly, each of the $\beta_2$- microglobulin gene and the IFN-$\gamma$R gene is inactivated for reducing or eliminating the expression of functional MHC antigens. The resulting cells may be used as universal donor cells. In addition, embryonic stem cells may be modified by homologous recombination for use in producing chimeric or transgenic mammalian hosts, which may be used as source of universal donor organs, or as models for drug and transplantation therapies. Methods for homologous recombination in non-transformed mammalian somatic cells are also described.

8 Claims, 12 Drawing Sheets

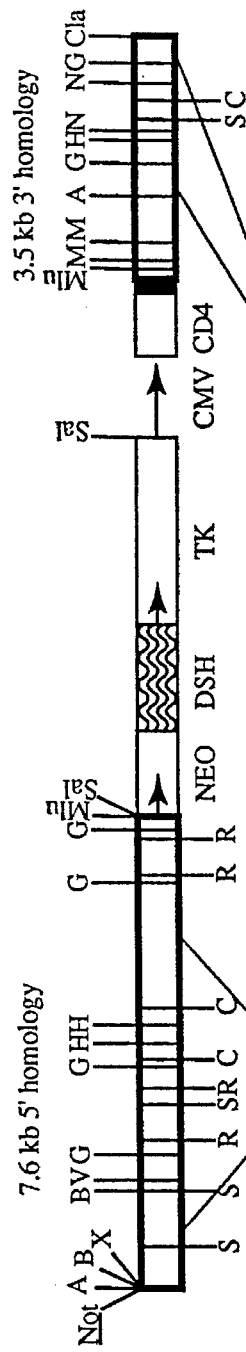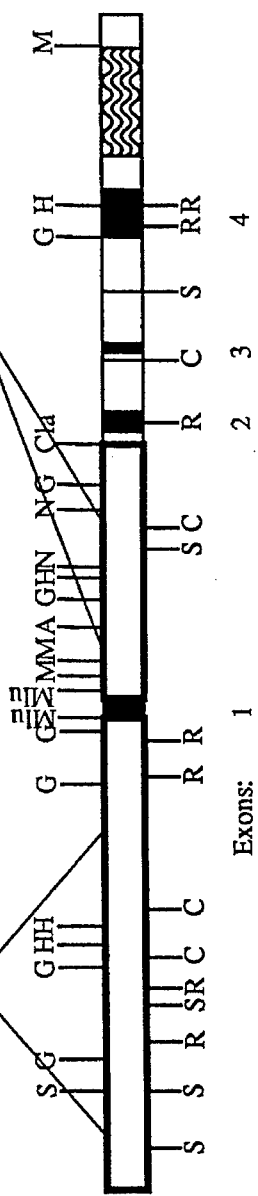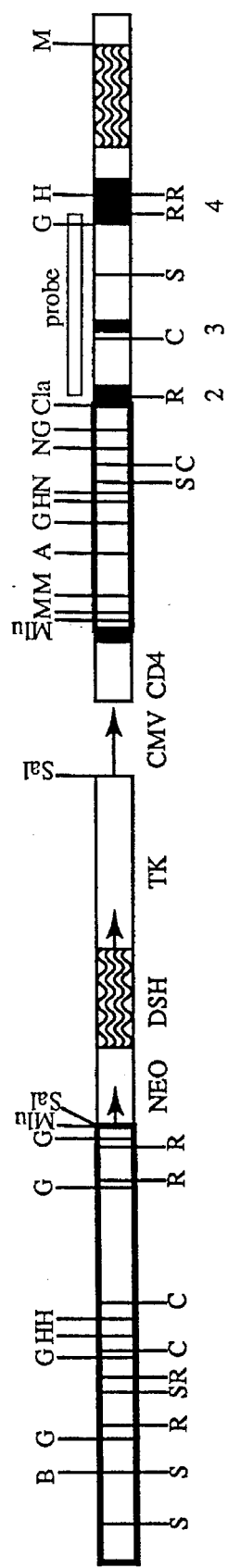
Figure 3a-c

148: β2-microglobulin gene trap vector

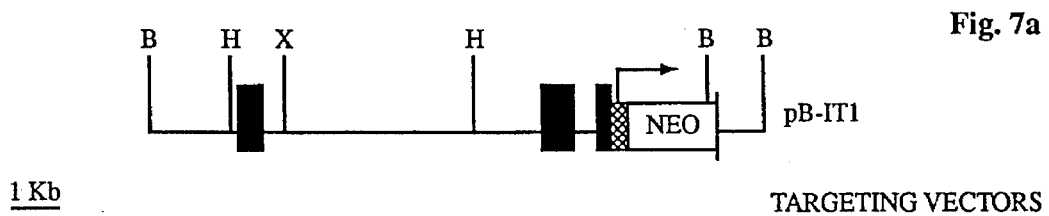
Fig. 7a
TARGETING VECTORS
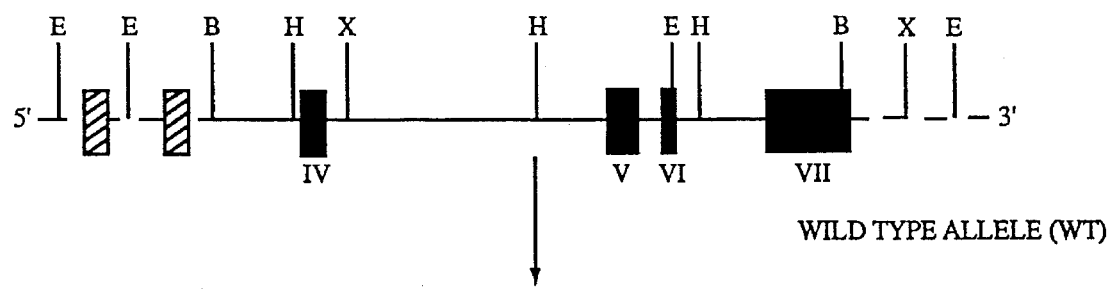
Fig. 7b
WILD TYPE ALLELE (WT)
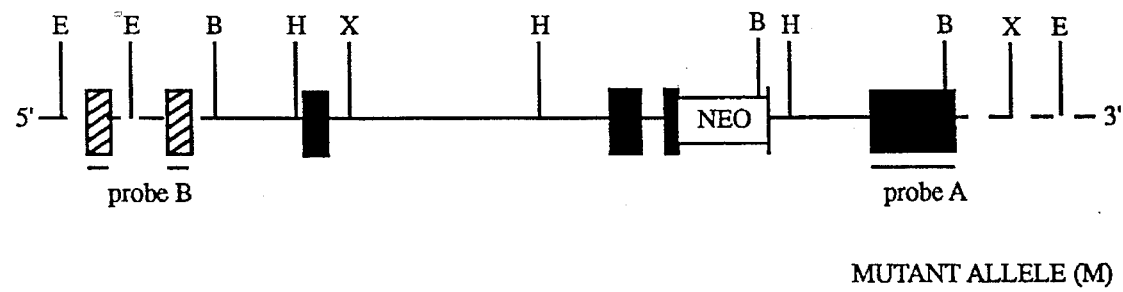
Fig. 7c
MUTANT ALLELE (M)
Fig. 7d
| | BamHI | XbaI | EcoRI | |
|---|---|---|---|---|
| | Probe A | Probe A | Probe A | Probe B |
| WT | 7.2 | 6.5 | 9.5 | 12.0, (6.5, 5.0)* |
| M | 2.5 | 7.5 | 22.5 | 22.5, (6.5, 5.0) |
Expected Fragment Lengths (Kb)
Figures 7a-7d

HOMOLOGOUS RECOMBINATION FOR UNIVERSAL DONOR CELLS AND CHIMERIC MAMMALIAN HOSTS

CROSS-REFERENCE TO GOVERNMENT GRANT

This application was made with grant number 5 P37 GM200069 awarded by the National Institutes of Health. The government may have certain rights in this invention.

CROSS-REFERENCE TO RELATED APPLICATIONS

This application is a continuation-in-part of application Ser. No. 990,879, filed Dec. 11, 1992, now U.S. Pat. No. 5,413,923 which was a continuation-in-part of application Ser. No. 611,020 filed Nov. 9, 1990, now U.S. Pat. No. 5,416,260 which was a continuation-in-part of application Ser. No. 431,872 filed Nov. 6, 1989, now abandoned and application Ser. No. 385,651, filed Jul. 25, 1989 now abandoned and claims priority to PCT/US90/04178, filed Jul. 25, 1990, the disclosures of which are all incorporated by reference herein.

INTRODUCTION

1. Technical Field

The field of the subject invention is the generation and use of major histocompatibility complex antigen lacking cells and organs lacking expression of functional major histocompatibility complex (MHC) antigen which may serve as universal donors in cellular and organ therapies including transplantation and to produce chimeric non-human mammals.

2. Background

To protect vertebrates from disease and infection, elaborate protective systems have evolved. In mammals, the immune system serves as the primary defense with many different types of cells and mechanisms to protect the host. A wide variety of hematopoietic cells exists, with the major protective lineages being lymphoid and myeloid. The immune system, which results from cells of the lymphoid and myeloid lineages is developed in vivo, so as to recognize self from non-self. Those aberrant situations where the immune system attacks self, such as rheumatoid arthritis, lupus erythematosus, and certain forms of diabetes, are evidence of importance to the host that only foreign agents be attacked. The protective mechanism which protects the host from disease, as a result of invasion of viruses, bacteria, or other pathogens, is also able to recognize cells which come from a different mammalian host, even an allogeneic host.

As part of the system for the self-versus-non-self recognition, the surface membrane protein major histocompatibility complex (MHC) antigens serve an important role. Each host has a personal set of Class I and II MHC antigens, which serve to distinguish that host from other hosts. The T-lymphoid system is predicated upon recognition of the presence of such MHC antigens as self. Where transplantation from another allogeneic host occurs, unless the transplant is matched with the host or the host is immunocompromised, the transplant may be attacked and destroyed by the immune system. When a transplant occurs which includes lymphocytes, monocytes or progenitors thereof, particularly bone marrow, a graft may attack the host as foreign, resulting in graft-versus-host disease.

There are many situations where one may wish to transplant cells into a recipient host where the recipient's cells are missing, damaged or dysfunctional. When the host is immunocompromised, there may be an interest in transfusing specific white cells, particularly T-cells, which may protect the host from various diseases. When the host lacks the ability to raise a defense against a particular disease, there may also be an interest in administering specific T-cells or B-cells or precursors thereof which may supplement the host's compromised immune system. In other cases, where certain cells are lacking, such as islets of Langerhans in the case of diabetes, or cells which secrete dopamine in the case of Parkinson's disease, or bone marrow cells in various hematopoietic diseases, or muscle cells in muscle wasting disease, or retinal epithelial cells in visual disorders, or keratinocytes for burns and non-healing wounds, it would be desirable to be able to provide cells which could fulfill the desired function. In order for the cells to be effective, they must be safe from attack by the host, so that they may function without being destroyed by the immune system. It is therefore of interest to find effective ways to produce cells which may function, proliferate, and differentiate as appropriate, while being safe from attack by a recipient's immune system, for example by the use of gene targeting to inactivate the expression of gene products that cause rejection of the transplanted cells. The same reasons apply to the use of organs for transplantation including but not limited to the heart, lung, liver and kidney.

Homologous recombination permits site-specific modifications in endogenous genes and thus inherited or acquired mutations may be corrected, and/or novel alterations may be engineered into the genome. The application of homologous recombination to gene therapy depends on the ability to carry out homologous recombination efficiently in normal diploid somatic cells. Homologous recombination or "gene targeting" in normal, somatic cells for transplantation represents a potentially powerful method for gene therapy, however, with the exception of pluripotent mouse embryonic stem (ES) cells, and continuous cell lines, homologous recombination has not been reported for a well-characterized, non-transformed, i.e "normal" mammalian somatic cell. In contrast to mouse ES cell lines, normal somatic human cells may have a finite life span in vitro (Hayflick and Moorhead, *Exptl. Cell. Res.* 25:585–621 (1961)). This makes their modification by gene targeting especially challenging, given the low efficiency of this process, i.e. $10^{-5}$ to $10^{-8}$ recombinants/input cell. Moreover, this process is further complicated by the fact that mammalian cells tend to integrate transfected DNA at random sites 100 to 1000 fold more efficiently than at the homologous site.

The present invention discloses methods for targeting non-transformed diploid somatic cells to inactivate genes associated with MHC antigen expression, including the $\beta_2$-microglobulin and IFN-$\gamma$R genes in cells such as retinal epithelial cells, keratinocytes and myoblasts. These methods provide novel targeting means for inactivating target genes resulting in lack of expression of functional MHC. In a method of the invention for targeting integral membrane proteins, the role of such proteins may be studied, and their expression manipulated, for example membrane proteins that serve as receptors, such as T cell receptors.

There is also substantial interest in being able to study various physiological processes in vivo in an animal model. In many of these situations, one would wish to have a specific gene(s) inactivated or introduced in a site-directed fashion. Where all or a substantial proportion of the cells present in the host would be mutated, the various processes could be studied. In addition, heterozygous hosts having one wild-type gene and one mutated gene could be mated to obtain homozygous hosts, so that all of the cells would have the appropriate modification. Such genetically mutated animals could serve for screening drugs, investigating physiologic processes, developing new products, and the like.

Relevant Literature

A number of papers describe the use of homologous recombination in mammalian cells, including human cells. Illustrative of these papers are Kucherlapati et al., *Proc. Natl. Acad. Sci. USA* 81:3153–3157, 1984; Kucherlapati et al., *Mol. Cell. Bio.* 5:714–720, 1985; Smithies et al., *Nature* 317:230–234, 1985; Wake et al., *Mol. Cell. Bio.* 8:2080–2089, 1985; Ayares et al., *Genetics* 111:375–388, 1985; Ayares et al., *Mol. Cell. Bio.* 7:1656–1662, 1986; Song et al., *Proc. Natl. Acad. Sci. USA* 84:6820–6824, 1987; Thomas et al., *Cell* 44:419–428, 1986; Thomas and Capecchi, *Cell* 51: 503–512, 1987; Nandi et al., *Proc. Natl. Acad. Sci. USA* 85:3845–3849, 1988; and Mansour et al., *Nature* 336:348–352, 1988.

Evans and Kaufman, *Nature* 294:146–154, 1981; Doetschman et al., *Nature* 330:576–578, 1987; Thomas and Capecchi, *Cell* 51:503–512, 1987; Thompson et al., *Cell* 56:316–321, 1989; individually describe various aspects of using homologous recombination to create specific genetic mutations in embryonic stem cells and to transfer these mutations to the germline. The polymerase chain reaction used for screening homologous recombination events is described in Kim and Smithies, *Nucleic Acids Res.* 16:8887–8903, 1988; and Joyner et al., *Nature* 338: 153–156, 1989. The combination of a mutant polyoma enhancer and a thymidine kinase promoter to drive the neomycin gene has been shown to be active in both embryonic stein cells and EC cells by Thomas and Capecchi, supra, 1987; Nicholas and Berg (1983) in *Teratocarcinoma Stem Cell*, eds. Siver, Martin and Strikland (Cold Spring Harbor Lab., Cold Spring Harbor, N.Y. (pp. 469–497); and Linney and Donerly, *Cell* 35:693–699, 1983.

Bare lymphocytes are described in Schuurman et al., The Thymocyte in "Bare Lymphocyte" Syndrome In: *Microenvironments in the Lymphoid System*, ed. Klaus, G.G.B., Plenum Press, N.Y., pp. 921–928 (1985); Sullivan et al., *J. Clin. Invest.* 76:75–79 (1985); Lisowska-Grospierre et al., ibid. 76:381–385 (1985); Arens, et al., *J. Inf. Dis.* 156:837–841 (1987); Clement et al. *J. Clin. Invest.*) 81:669–675 (1988); Sugiyama et al., *Chest* 89:398–401 (1986); and Hume et al., *Human Immunology* 25:1–11 (1989).

Transplantation of various normal somatic cells to treat hereditary disease has been reported (Blaese et al., *Human Gene Ther.* 4:521–527 (1993)). Recent transplantation experiments suggest that myoblast transplantation represents a potentially useful vehicle for drug delivery (Barr et al., *Science* 254:1507–1509 (1991) and Dhawan et al., *Science* 254:1509–1512 (1991)). For example, transplantation of normal myoblasts to treat Duchenne muscular dystrophy and other muscle degeneration and wasting diseases has been proposed by Partridge, *Muscle & Nerve* 14:197–212 (1991).

Interferon-gamma (IFN-γ) is a cytokine that is produced during the process of infection and inflammation which exhibits potential antiviral, anti-proliferative and immunomodulatory effects (Trinchieri et al., *Immunol. Today.* 6:131–136 (1985); Pestka et al., *Ann. Rev. Biochem.* 56:727–777 (1987); and Farrar et al., *Ann. Rev. Immunol.* 11:571–611 (1993)). Many of these actions are thought to be mediated by binding to a ubiquitously expressed, high affinity cell surface receptor, the IFN-γ receptor, (Aguet et al., *Cell* 55:273–280 (1988)) which triggers the induction of MHC antigens (Rosa et al., *Immunol. Today* 5:261–262 (1984)). Because IFN-γ upregulates the expression of the products of the genes encoding $\beta_2$-microglobulin and the transporter of the antigenic peptides TAP-1 and TAP-2 associated with expression of MHC Class I complex (Germain et al., *Ann. Rev. Immunol.* 11:403–450 (1993)), as well as expression of MHC Class I and II molecules (Pestka et al., *Ann. Rev Biochem.* 56:727–777 (1987); Farrar et al., *Ann. Rev. Immunol.* 11:571–611 (1993); Rosa et al., Immunol. Today 5:262–262 (1984) and Trowsdale et al., *Nature* 348:741–744 (1990)), blocking the effects of IFN-γ by inactivating its receptor using homologous recombination may decrease cellular rejection of allogeneic transplants. Cultured human myoblasts express both MHC Class I and Class II antigens at very low levels, but their expression increases significantly after treatment with IFN-γ (Bao et al., *Immunol. Cell Biol.* 68:235–242 (1990)). Thus, in an allogeneic recipient, IFN-γ released by T cells infiltrating the transplantation site may upregulate MHC expression, resulting in rejection of the donor myoblasts. As the expression of MHC Class I can also be upregulated by other cytokines such as IFN-α and IFN-β and IL-1, inactivation of the IFN-γR may be combined with inactivation of other genes important for MHC Class I expression, for example, IL-1R, TAP 1 and/or TAP 2 and/or $\beta_2$-microglobulin and/or proteasome genes, to produce universal donor myoblasts that may be transplanted across histocompatibility barriers.

Schwartzberg et al. *Proc. Natl. Acad. Sci. USA* 87:3210–3214 (1990) describe a targeted gene disruption of an endogenous c-abl locus by homologous recombination with DNA encoding a selectable fusion protein. Other references of interest include Jasin et al., *Genes & Development* 4:157–166 (1990) describing gene targeting at the human CD4 locus by epitope addition and Doetschman et al., *Proc. Natl. Acad. Sci. (USA)* 85:8583–8587 (1988) which describe targeted mutation of the Hprt gene in mouse embryonic stem cells using a targeting DNA fragment containing a promoterless neo gene. Other references describing various uses of the Neo gene in targeting include Sedivy and Sharp, *Proc. Natl. Acad. Sci. (USA)* 86:227–231 (1989); Riele et al, *Letters to Nature* 348:649–651 (1990); Jeannotte et al., *Molec. and Cell. Biol.* 11(11):5578–5585 (1991); Charron et al., *Molec. Cell. Biol.* 10 (4):1799–1804 (1990); Stanton et al., *Molec. Cell. Biol.* 10(12):6755–6758 (1990).

The successful application of gene targeting to somatic cell gene therapy requires the precise integration of exogenous DNA into the target locus without inducing other genetic alterations resulting in phenotypic abnormalities in the target cell. There exists an ongoing need for methods which enrich for the lower frequency recombinant events that occur in somatic cells as compared to the frequency of random recombination.

SUMMARY OF THE INVENTION

Mammalian cells lacking at least one functional major histocompatibility complex: (MHC) antigen are provided which may serve to diminish immune attack when used for transplantation, particularly as universal donor cells, including non-transformed diploid human somatic cells, or as embryonic stem cells which may be used to produce chimeric mammals carrying the mutation. The cells are obtained as a result of homologous recombination. Particularly, by inactivating at least one allele of at least one MHC antigen chain, e.g., a MHC α chain, or β$_2$-microglobulin, cells can be produced which have reduced capability for expression of functional MHC antigens. The resulting cells lacking functional MHC antigen may be used as donors for transplantation lacking markers for host (recipient) immune attack. The cells may be used to produce tissue for transplantation. The cells, may also be used in vitro to interact with other cells. Transgenic mammals carrying this trait may be used in the study of immunodeficiency and may be used as a source of tissues and cells for transplantation.

Alternatively, cells containing inactivated genes associated with the expression of MHC antigen for example the IFN-γR gene, are obtained using the methods of the invention, to prevent the upregulation of MHC antigen expression in response to IFN-γ, resulting in the generation of donor cells deficient in the ability to upregulate expression of MHC antigen.

Methods and targeting constructs are provided wherein low frequency homologous recombination in non-transformed somatic cells may be rapidly detected. In a method of the invention, a DNA construct containing a strong promoter and an epitope that binds to a ligand for detection, and a selectable marker gene is targeted to a sequence in the chromosome of a cell encoding the target locus for homologous recombination. When this DNA construct is transfected into cells, a fusion protein is expressed and secreted outside of the cell. Additionally, novel methods and targeting constructs are provided for inactivation of integral membrane proteins by inserting a selectable marker gene into the protein coding region downstream from a sequence encoding a leader sequence and a transmembrane sequence. The targeting construct inserts the selectable maker gene into the gene encoding the integral membrane protein so as to be in reading frame with the upstream sequence and to encode a fusion protein with the marker on the cytoplasmic side, of the membrane and functional. Cells are transformed with the constructs using the methods of the invention and are selected by means of the selectable marker and then screened for the presence of recombinants.

Another method of the invention is for determining the effectiveness of a therapeutic agent to prevent transplant rejection in a mammal, by administering a therapeutic agent such as cyclosporine to the mammal into which tissues or cells that lack expression of functional MHC antigen have been transplanted, and observing for the presence or absence of rejection of the transplanted tissues or cells over time.

BRIEF DESCRIPTION OF THE DRAWINGS

FIG. 3A–C is a diagram of the #137 targeting vector (FIG. 3A), the human β$_2$-M locus (FIG. 3B) and the correctly targeted recombinant locus (FIG. 3C), described in Example V, infra.

FIG. 7 A–C depicts the strategy for targeting the mouse IFNγR gene, as described in Example VIII, infra: FIG. 7A diagrams the IFNγR targeting vectors pB-IT1 and pB-IT2 (stippled box in pB-IT1 indicates the promoter-enhancer sequences of MCl-Neo poly A); FIG. 7B shows the partial restriction map of the wild type IFNγR gene (solid line=the BamHI fragment; black boxes=exons; dashed lines=sequences outside the BamHI fragment) FIG. 7C shows the predicted structure of the target locus following homologous recombination (cross-hatched boxes=IFNγR sequences hybridizing with probe B; B=BamHI; H=HindIII; E=EcoRI and X=XbaI).

FIG. 7D shows the expected sizes of restriction fragments on Southern analysis of wild-type and targeted loci.

FIG. 9 A–B are fluorescence profiles indicating expression of antigens in mouse myoblasts as described in Example VIII, infra.

FIG. 10 A–C shows the results of analyses of morphology, differentiation and chromosome analysis of targeted mouse myoblasts (IFNγR, +/–) as described in Example VIII, infra.

DESCRIPTION OF SPECIFIC EMBODIMENTS

Figure 1:
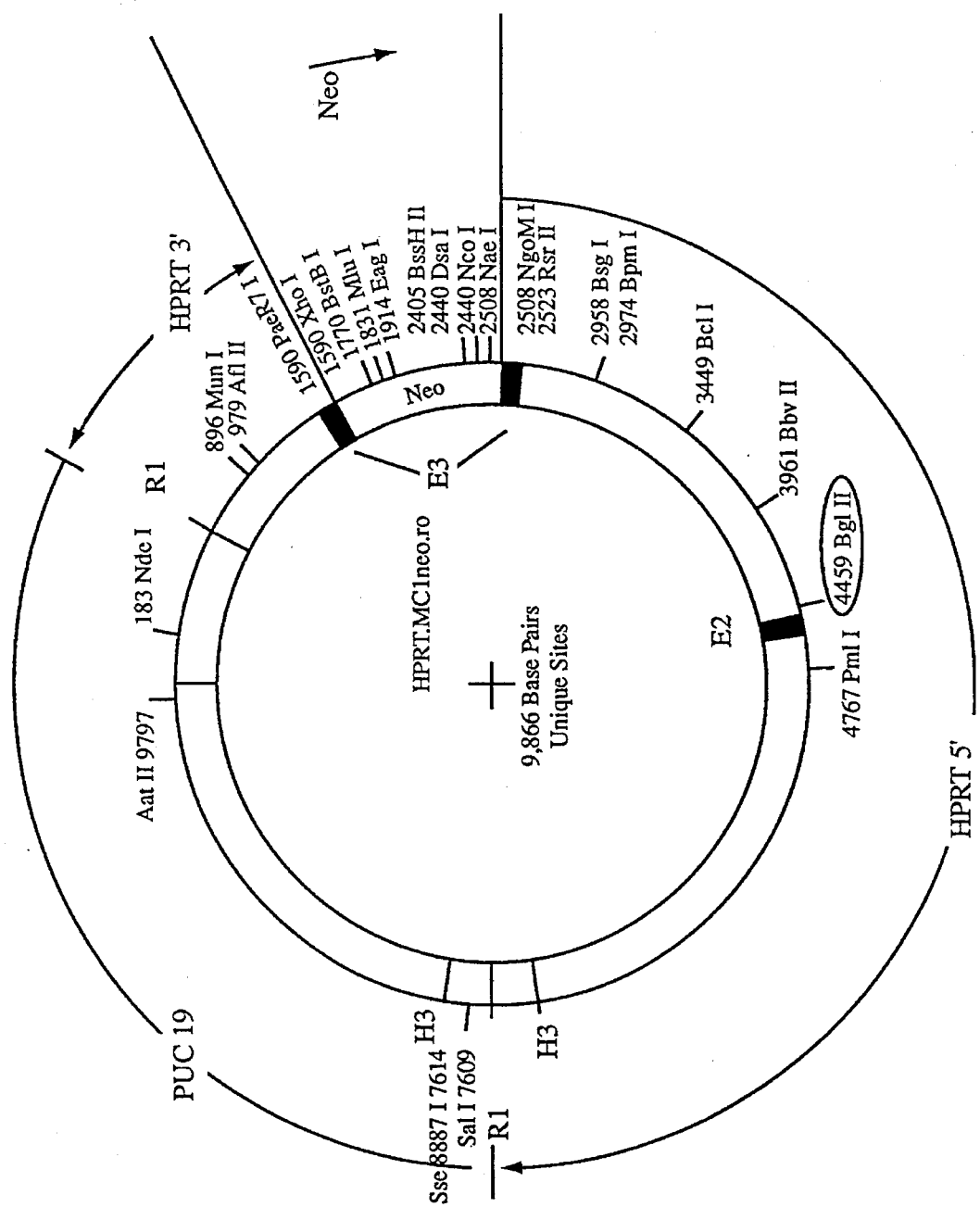
FIG. 1 depicts vector HPRT.MClneo.ro as described in Example IV, infra (R1=fragment of human HPRT gene).

Genetically engineered mammalian cells lacking functional MHC antigens are provided for a variety of purposes such as universal donor cells for transplantation. The cells are obtained as a result of homologous recombination. The cells may be further modified by introduction or inactivation of a gene of interest.

The modified cells may be used to generate transgenic animals, which have reduced expression of MHC antigens in all tissues and organs. Such animals, particularly mice and other small mammals, may be used experimentally to determine the effect of an agent, particularly to screen drugs. They may be used as a model system for various transplantation therapies, including transplants of skin, kidney, liver, etc.

Homologous recombination may be employed for inactivation or alteration of genes in a site-directed manner, particularly a gene associated with an MHC antigen. Depending upon the nature of the cell, the cell lacking at least one functional MHC antigen may find use as a donor to an allogeneic host or if an embryonic stem cell, may find use in the production of transgenic mammalian hosts which themselves could be used as a source of organs or cells or tissues for transplantation.

The Class I and Class II MHC antigens are heterodimers, each consisting of an α and a β subunit. In Class I MHC antigens, the β subunit is $\beta_2$-microglobulin. Of particular interest is the inactivation of at least one, preferably both, copies of a subunit of an MHC antigen, more particularly, $\beta_2$-microglobulin. Where a mutation in the $\beta_2$-microglobulin gene of an embryonic stem cell is produced, a mammalian host derived from the embryonic stem cell may be used for investigation of the immune system and the role of Class I MHC antigen in that system. Of particular interest are methods which provide for cells lacking at least one functional MHC antigen, Class I or Class II, preferably Class I, which cells may serve a variety of functions in a viable host. The method involves transfection of mammalian cells, particularly normal cells, of a predetermined species with DNA associated with one of the loci related to the $\beta_2$-microglobulin gene, the α-subunit(s) of the Class I or II MHC antigens of the β-subunit(s) of the Class II MHC antigens. The human Class II MHC antigens are HLA-DR, DP AND DQ, where DR is of primary interest.

The DNA will comprise at least a portion of the gene(s) at the particular locus with introduction of a lesion into at least one, usually both copies, of the native gene(s), so as to prevent expression of a functional MHC antigen molecule. The lesion may be ant insertion, deletion, replacement or combination thereof. When the lesion is introduced into only one copy of the gene being inactivated, the cells having a single unmutated copy of the target gene are amplified and may be subjected to a second targeting step, where the lesion may be the same or different from the first lesion, usually different, and where a deletion, or replacement is involved, may be overlapping at least a portion of the lesion originally introduced. In this second targeting step, a targeting vector with the same arms of homology, but containing a different mammalian selectable marker, for example hygromycin resistance ($hyg^r$) is used to produce a homozygously targeted clone (targeting efficiency of approximately $10^{-5}$ to $10^{-8}$). The resulting transformants are screened for the absence of a functional target antigen and the DNA of the cell may be further screened to ensure the absence of a wild-type target gene. Alternatively, homozygosity as to a phenotype may be achieved by breeding hosts heterozygous for the mutation.

Alternatively, one can select for cells that have spontaneously become homozygous. Thus, cells may lose the wild-type, unaltered copy of the locus on the non-targeted chromosome for example by non-disjunction in heterozygous cells. This results during cell division from incorrect sorting of the four sets of chromosomes in a normal diploid somatic cell or ES cell. Normally the cell sorts one copy of each chromosome into each of two daughter cells during cell division. On occasion (frequencies of about $10^{-5}$) the cell will sort two copies of the same chromosome into one of the daughter cells and both copies of the other chromosome into the other daughter cell. Most of the time this mechanism will produce a normal viable cell containing two copies of the altered gene. A different mechanism producing a homozygous cell spontaneously during cell division is gene conversion. At low frequencies (less than $10^{-6}$) a cell will edit a gene using its homolog as the editing template. This is essentially a recombination event in which the differences between two similar genes are removed (edited out). This editing occurs over a short region (from 1 to 1000 bp) and will produce homozygotes. In the present invention, a homozygous clone will no longer express functional MHC antigen because it no longer expresses any of the targeted gene product. For example, a cell will no longer express functional Class I MHC when it is homozygous for the inactivated $\beta_2$-microglobulin gene. The heterozygous cells can then be selected against using a combination of anti-MHC Class I antibodies and complement or using a combination of the antibodies and magnetic beads (Vaccaro, *Am. Biotech. Lab.* 30–35 (1990)) or FACS sorting. In addition, because in heterozygous cell there is only a single copy of the resistance gene, e.g. $neo^r$, while in a homozygous clone there are two copies of this gene, decreasing the efficiency of the resistance gene, e.g. via a mutation in the Neo sequence or the promoter, permits selection of concentrations of the selection agent, e.g. G418, favoring the growth of the homozygous cells containing two copies (Mortensen et al., *Mol. Cell. Biol.* 12 (5):2391–2395 (1992)). In addition, because non-disjunction is a reciprocal event, and the homozygous wild-type cell is very sensitive to antibiotic selection, low level antibiotic selection will cause a population to drift towards homozygosity during continuous expansion of the cell population.

The cells which may be subjected to transformation may be any mammalian cells of interest, which may find use in cell therapy, research, interaction with other cells vitro or the like. Cells of particular interest include, among other lineages, the islets of Langerhans, adrenal medulla cells which may secrete dopamine, osteoblasts, osteoclasts, epithelial cells, endothelial cells, T-lymphocytes, neurons, glial cells, ganglion cells, retinal cells, embryonic stem cells, liver cells, bone marrow cells, and myoblast (muscle) cells. The cells may be obtained from any mammalian host, including murine and other rodents, lagomorphs, porcine, feline, bovine, canine, human, etc.

The cells lacking functional MHC expression will be selected to achieve a particular function and be introduced into a mammalian host or used for research or other purpose. Also of interest will be the stem cells which act as the progenitors for any of the above cells, which may be the original progenitor or a progenitor cell which is already dedicated to a particular lineage. Of particular interest will be non-transformed diploid mammalian somatic cells, particularly human cells, including epithelial cells, such as keratinocytes, retinal epithelial cells, and mesenchymal cells such as myoblasts, hematopoietic cells, lymphocytes such as T cells, and other cells which may be readily manipulated in vitro, maintained for long periods of time in culture and may be introduced into a host, where the cells will remain viable and functional for extended periods of time.

For embryonic stem cells, an embryonic stem cell line may be employed or embryonic stem cells may be obtained freshly from a host such as a murine animal, e.g. a mouse, rat, guinea pig, chinese hamster or other small laboratory animals. The cells may be grown on an appropriate fibroblast-feeder layer or grown in the presence of leukemia inhibiting factor (LIF) and then used for mutation.

The procedures employed for inactivating one or both copies of a gene associated with a particular MHC antigen to produce cells lacking expression of functional MHC antigen will be similar, differing primarily in the choice of sequence, selectable marker used, and the method used to identify the absence of the MHC antigen, although similar methods may be used to ensure the absence of expression of a particular antigen. Since the procedures are analogous, the inactivation of the $\beta_2$-microglobulin gene, and the IFN-γR gene are used as examples. It is to be understood that substantially the same procedures, but with other genetic sequences, will suffice for the α- and β-subunits of the Class II MHC antigens, and for other genes associated with functional MHC antigen expression.

DNA constructs may be employed which provide for the desired introduction of the lesion into the cell. The constructs may be modified to include functional entities other than the mutated sequence which may find use in the preparation of the construct, amplification, transfection of the host cell, and integration of the construct into the host cell. Techniques which may be used include calcium phosphate/DNA coprecipitates, microinjection of DNA into the nucleus, electroporation, bacterial protoplast fusion with intact cells, transfection, or the like. The DNA may be single or double stranded, linear or circular, relaxed or supercoiled DNA. For various techniques for transfecting mammalian cells, see Keown et al., *Methods in Enzymology* (1990) Vol. 185, pp. 527–537.

The homologous sequence for targeting the construct may have one or more deletions, insertions, substitutions or combinations thereof. For example, the $\beta_2$-microglobulin may include a deletion at one site and an insertion at another site which includes a gene which may be used for selection, where the presence of the inserted gene will result in a defective inactive protein product. Preferably, substitutions are employed. For an inserted gene, of particular interest is a gene which provides a marker, e.g., antibiotic resistance such as neomycin resistance, including G418 resistance.

The deletion will be at least about 50 bp, more usually at least about 100 bp, and generally not more than about 20 kbp, where the deletion will normally include at least a portion of the coding region including a portion of or one or more exons, a portion of or one or more introns, and may or may not include a portion of the flanking non-coding regions, particularly the 5'-non-coding region (transcriptional regulatory region). Thus, the homologous region may extend beyond the coding region into the 5'-non-coding region or alternatively into the 3'-non-coding region. Insertions will generally not exceed 10 kbp, usually not exceed 5 kbp, generally being at least 50 bp, more usually at least 200 bp.

The homologous sequence should include at least about 100 bp, preferably at least about 150 bp, more preferably at least about 300 bp of the target sequence and generally not exceeding 20 kbp, usually not exceeding 10 kbp, preferably less than about a total of 5 kbp, usually having at least about 50 bp on opposite sides of the insertion and/or the deletion in order to provide for double crossover recombination.

Upstream and/or downstream from the target gene construct may be a gene which provides for identification of whether a double crossover has occurred. For this purpose, the herpes simplex virus thymidine kinase gene may be employed, since the presence of the thymidine kinase gene may be detected by the use of nucleoside analogs, such as Acyclovir or Gancyclovir, for their cytotoxic effects on cells that contain a functional HSV-tk gene. The absence of sensitivity to these nucleoside analogs indicates the absence of the thymidine kinase gene and, therefore, where homologous recombination has occurred that a double crossover event has also occurred.

The presence of the selectable marker gene inserted into the $\beta_2$- microglobulin gene establishes the integration of the target construct into the host genome. However, DNA analysis will be required in order to establish whether homologous or non-homologous recombination occurred. This can be determined by employing probes for the insert and then sequencing the 5' and 3' regions flanking the insert for the presence of $\beta_2$-microglobulin extending beyond the flanking regions of the construct or identifying the presence of a deletion, when such deletion is introduced.

The polymerase chain reaction may be used with advantage in detecting the presence of homologous recombination. Primers may be used which are complementary to a sequence within the construct and complementary to a sequence outside the construct and at the target locus. In this way, one can only obtain DNA duplexes having both of the primers present in the complementary chains if homologous recombination has occurred. By demonstrating the presence of the primer sequences or the expected size sequence, the occurrence of homologous recombination is supported.

The construct may further include a replication system which is functional in the mammalian host cell. For the most part, these replication systems will involve viral replication systems, such as Simian Virus 40, Epstein-Barr virus, papilloma virus, adenovirus and the like.

Where a marker gene is involved, as an insert, and/or flanking gene, depending upon the nature of the gene, it may have the wild-type transcriptional regulatory regions, particularly the transcriptional initiation regulatory region or a different transcriptional initiation region. Whenever a gene is from a host where the transcriptional initiation region is not recognized by the transcriptional machinery of the mammalian host cell, a different transcriptional initiation region will be required. This region may be constitutive or inducible, preferably inducible. A wide variety of transcriptional initiation regions have been isolated and used with different genes. Of particular interest as promoters are the promoters of metallothionein-I and II from a mammalian host, thymidine kinase, $\beta$-actin, immunoglobulin promoter, human cytomegalovirus promoters, SV40 promoters and polyoma virus promoters. In addition to the promoter, the wild type enhancer may be present or an enhancer from a different gene may be joined to the promoter region.

The construct may further include a replication system for prokaryotes, particularly *E. coli*, for use in preparing the construct, cloning after each manipulation, allowing for analysis, such as restriction mapping or sequencing, followed by expansion of a clone and isolation of the plasmid for further manipulation. When necessary, a different marker may be employed for detecting bacterial transformants.

Once the vector has been prepared, it may be further manipulated by deletion of the bacterial sequences as well as linearization, where a short deletion may be provided in the homologous sequence, generally not exceeding about 500 bp, generally being from about 50 to 300 bp. The small deletion will generally be near one or other end of the targeted structural gene.

Once the construct has been prepared and manipulated and the undesired sequences removed from the vector, e.g., the undesired bacterial sequences, the DNA construct is now ready to be introduced into the target cells. As already indicated, any convenient technique for introducing the DNA into the target cells may be employed. After transformation of the target cells, many target cells are selected by means of positive and/or negative markers, as previously indicated, neomycin resistance and Acyclovir or Gancyclovir resistance. Those cells which show the desired phenotype may then be further analyzed by restriction analysis, electrophoresis, Southern analysis, polymerase chain reaction or the like. By identifying fragments which show the presence of the lesion(s) at the target gene site, one can identify cells in which homologous recombination has occurred to inactivate one of the two copies of the target gene.

The second construct will differ from the first construct in not necessarily requiring a marker for selection, since the absence of the target MHC antigen on the surface of the cells may be used as a marker. Thus, one may again use insertions, deletions or replacements as lesions for modifying and inactivating the target gene. Similarly, one may detect the absence of a Class II MHC antigen on the surface as evidence of the absence of expression of the particular Class II MHC antigen.

In a method of the invention for inactivating a gene associated with expression of functional MHC antigen in non-transformed human somatic cells, cells in which the target gene is correctly targeted are identified using novel targeting vectors and an ELISA-based detection system, permitting the rapid detection of numerous independently targeted clones. In this method a site for homologous recombination is designed to create a recombinant fusion protein driven by a strong enhancer/promoter, for example the CMV enhancer, fused to the domain of a protein containing an epitope, such as CD4, that can be detected by a ligand to which it binds, for example an antibody, where the recombinant fusion protein is secreted by a correctly targeted cell and is then detected using an ELISA-based system employing antibodies that recognize the secreted fusion protein. In this method, the 5' end of the recombinant locus is derived from the targeting vector, while the 3' end of the locus is derived from the target gene. Because the entire 5' end is controlled experimentally, both the recombinant fusion protein's expression level and ultimate transport fate can be directed. In the examples below, human retinal pigmented epithelial (RPE) cells and human keratinocytes were genetically engineered to express a CD4-$\beta_2$-microglobulin fusion protein to facilitate detection of the recombinants. Media is screened to detect the fusion protein in an ELISA which traps proteins containing a $\beta_2$-microglobulin epitope and detects proteins containing a CD4 epitope. The assay was shown to be specific for the CD4$\beta_2$-microglobulin fusion protein, allowing detection of as few as 1000 expressing cells. This method may be used for other mammalian cell types, including ES cells. In addition to a CD4 epitope other peptides that contain an epitope recognized by a ligand such as an antibody that binds to the epitope may be used in the fusion protein.

In another method of the invention, somatic cells are engineered to inactivate genes associated with functional MHC antigen expression. In this method, a promoterless selectable marker gene is fused in reading frame with the upstream sequence of the target gene to the transmembrane domain of an integral membrane protein producing in fusion protein. The fusion protein is transported to the membrane and processed to provide the transmembrane sequence, normal external membrane protein and the selectable marker positioned on the cytoplasmic side of the membrane. Cells into which the DNA construct has been introduced and in which homologous recombination has occurred to provide the fusion protein are grown under selective conditions to obtain a population of cells containing the marker and where one of the target genes has been inactivated. This results in a higher frequency of detection of gene targeting events (higher frequency per Neo resistant colony as compared to the frequency of targeting obtained using a Neo-gene with its native promoter).

After integration, the cell will comprise a gene for the fusion protein comprising in the 5' to 3' direction of transcription, the wild-type transcriptional initiation region, the initiation codon, the sequence encoding the extracellular region and the transmembrane region of the integral membrane protein, any introns present, the selectable marker gene (including stop codons) which may be separated from the sequence encoding the transmembrane region by an intron, where appropriate donor and acceptor splice sites are present for joining the selectable marker gene to the transmembrane domain encoding sequence, and/or a portion, all or none of the sequence encoding the intracellular (cytoplasmic) domain of the integral membrane protein, and a transcriptional termination region, either joined to the selectable marker gene or the wild-type transcriptional termination region of the target gene.

Any integral membrane protein may be targeted, including cluster or differentiation "CD" antigens. Of particular interest are MHC antigens, T cell receptors and subunits, e.g. $\alpha$, $\beta$, $\eta$, $\zeta$, and various receptor proteins including interferon receptors, neurotransmitter receptors, growth factor receptors, colony stimulating factor receptors, etc.

In the examples below, mouse ES cells and mouse myoblasts were engineered to inactivate the IFN-$\gamma$R gene to prevent upregulation of MHC expression. The targeting vector employed contained a transcriptionally and translationally impaired selectable marker gene (neomycin) inserted into the IFN-$\gamma$R coding region. Upon homologous recombination, the selectable marker Neo was expressed as an IFN-$\gamma$R-Neo hybrid protein in which Neo, fused to the transmembrane domain of the IFN-$\gamma$R, is situated in the inner surface of the cytoplasmic membrane, protecting the recombinants from antibiotic (G4 18) killing. Other selectable marker genes may be used such as the hygromycin resistance gene (hyg$^r$), and any integral membrane protein may be targeted.

Transformation of the cells in which one of the copies of the MHC gene has been inactivated may then be performed in the same or different way from the previous method of transformation to produce cells homozygous for the inactivated MHC gene. The resulting transformed cells may then be selected by the absence of the target MHC antigen on the surface of the cell. This can be achieved in a variety of ways. For example, one may use antibodies to any epitope of the target MHC antigen in conjunction with complement to kill any cells having the antigen. Alternatively, one may use conjugates of the appropriate antibody, particularly monoclonal antibody with a toxin, such as the A chain of ricin, abrin, diphtheria toxin, or the like. Affinity chromatography may be employed, where antibodies may be used to remove cells expressing the target antigen. The resulting cells which survive should be free of at least one MHC antigen on their surface and now not be subject to transplant rejection when introduced in vivo as wild-type cells.

The resulting cells will then be screened to ensure that substantially no Class I MHC antigens are on the surface. This may be achieved as described above by selecting for cells lacking the Class I MHC antigen. The cells may then be grown in an appropriate nutrient medium for expansion and used in a variety of ways. The cells may be used for transplantation, to become part of an existing tissue, or may be grown to form tissue for transplantation into a non-syngeneic host. For example, with keratinocytes, the cells may be used for replacement of skin in the case of burns, where keratinocytes may be grown to form a continuous layer prior to application. Similarly, the keratinocytes may be used in the case of plastic surgery to replace skin removed from the host for use at another site. Other uses for the keratinocytes include transplantation in decubitus and other non-healing ulcers.

In the case of islets of Langerhans, they may be grown and introduced into capsules or otherwise for insertion into a host for the production of insulin. In the case of retinal epithelial cells, they may be injected or implanted into the subretinal space of the eye to treat visual disorders, such as macular degeneration. In the case of immune cells, they may be injected into the bloodstream or elsewhere to treat immune deficiency. In the case of myoblasts, they may be injected at various sites to treat muscle wasting diseases, such as Duchenne muscular dystrophy. For organ transplants, non-syngeneic tissue such as xenogeneic grafts of heart or liver may be performed between related species.

The genes which are introduced may also serve for protein production, where the proteins may be retained intracellular or be secreted. Production of proteins may include growth factors such as, e.g., G-, M-, and GM-CSF, epidermal growth factor, platelet derived growth factor, transforming growth factor, etc; lymphokines, such as the interleukins; hormones, such as ACTH, somatomedin, insulin, angiotensin, etc., coagulation factors, such as Factor VIIIC; normal versions of the proteins associated with genetic diseases such as adenosine deaminase or the protein associated with cystic fibrosis; protective agents, such as α1-antitrypsin; regulatory proteins or enzymes associated with the production of amino acid free products, such as the expression of tyrosine hydroxylase for the production of L-dopamine, and the like. The genes may be under the transcriptional control of a constitutive promoter or inducible promoter (including enhancer sequence). In the latter situation, regulation may result by induction by a naturally occurring signal or as a result of introduction into the host of an exogenous signal.

Depending upon the nature of the cells, the therapy involved, and the disorder, the cells may be employed as films, introduced in containers for maintenance at a particular site, or as solid masses impregnated in inert matrices or independent of a matrix, or as cell suspensions in the case of lymphocytes, leukocytes or blood cells. The number of cells administered will vary widely, depending upon the particular application and the manner in which the cells are administered. Administration may be by injection, topical application, incision and placement, in the appropriate location.

When embryonic stem cells, particularly ES cells from a murine host, have been transformed, it may be desirable to use such cells to grow transgenic animals. For such a procedure, after mutation the cells may be plated onto a feeder layer in an appropriate medium, e.g., fetal bovine serum enhanced DMEM. Cells containing the construct may be detected by employing a selective medium and after sufficient time for colonies to grow, colonies may be picked and analyzed for the occurrence of homologous recombination. As described previously, the polymerase chain reaction may be used, with primers within and without the construct sequence but at the target locus. Those colonies which show homologous recombination may then be used for embryo manipulating and blastocyst injection. Blastocysts may be obtained from 4 to 6 week old superovulated females by flushing the uterus 3.5 days after ovulation. The embryonic stem cells may then be trypsinized and the modified cells added to a droplet containing the blastocysts. At least one, usually at least about 10, and up to about 30 of the modified embryonic stem cells may be injected into the blastocoel of the blastocyst. After injection, at least one and not more than about 15 of the blastocysts are returned to each uterine horn of pseudopregnant females. Females are then allowed to go to term and the resulting litters screened for mutant cells having the construct. The blastocysts are selected for different parentage from the transformed ES cells. By providing for a different phenotype of the blastocyst and the ES cells, chimeric progeny can be readily detected. A particularly useful phenotype is hair color, although any phenotype may be used or, if desired, one may look to genotype, probing for the presence of the modified genomic DNA.

The pups will usually be born 16–18 days after introduction of the blastocysts into foster mothers. The chimeric animals are screened for the presence of the transformed genome and males and females comprising the transformed genome are mated. The homozygous progeny lack functional Class I MHC cells and have reduced numbers of mature CD8$^+$T-cells (TCR αβ).

The transgenic mammals may be any non-human mammal, such as laboratory animals, domestic animals, etc. Such mammals may be murine and other rodents, lagomorphs, porcine, feline, bovine, canine, human, etc. The mammals which lack Class I MHC may be used as a source of organs, cells or tissues for transplantation, such as heart, lung, skin, liver and kidney. The animals may also be used experimentally to screen drugs, for example to monitor rejection of transplants in the animals in the presence of a therapeutic agent such as an immunosuppressive agent, e.g. cyclosporine, or as a model system for transplantation therapies, including transplants of skin, kidney, liver, etc.

In the experimental section below, embodiments are disclosed which demonstrate the production of cells lacking expression of functional MHC antigen as a result of inactivation of various genes associated with MHC antigen expression using homologous recombination. Thus, in a first embodiment, the method is described for inactivating the $\beta_2$-microglobulin gene in mouse and human keratinocytes using the methods of the invention.

In a further embodiment, mouse embryonic stem cells containing inactivated $\beta_2$microglobulin and mice generated from these cells are described. Translation of MHC-deficient mouse skin cells is disclosed in another embodiment.

In a still further embodiment, targeting of the HPRT gene in human retinal epithelial cells (RPE) is described.

In another embodiment, targeting of the $\beta_2$-microglobulin gene in human RPE cells using a targeting vector producing a fusion protein recombinant is disclosed. In a further embodiment use of a simple Neo replacement targeting vector to inactivate the $\beta_2$-microglobulin gene is described.

In still another embodiment, targeting of the IFN-γR gene in mouse embryonic stem cells and mouse myoblasts using targeting vectors containing a promoterless selectable marker gene is described.

The following examples are offered by way of illustration and not by way of limitation.

EXPERIMENTAL

I. Proliferation of epidermal keratinocytes lacking MHC antigen due to inactivation of $\beta_2$-microglobulin gene expression.

Cells

Mouse epidermal keratinocytes are obtained from the skin of a newborn mouse. The skin samples are rinsed in serum-free medium and minced into small fragments. The fragments are treated with trypsin and the resulting single cell suspension washed and plated on 3T3 fibroblast feeder layers. EGF (5 ng/ml) is added at the end of five days. The cells are maintained in media supplemented with hydrocortisone ($10^{-6}$M), cholera toxin ($10^{-7}$M), insulin (5 ng/ml), transferrin (5 ng/ml), T3 ($2\times10^{-8}$M) and 20% fetal calf serum. Unused cells are stored in liquid nitrogen.

Human epidermal keratinocytes are isolated using a fresh skin sample from a circumcised skin as the source of the keratinocytes. The sample is then treated substantially as described above.

DNA Vectors

The mouse and human $\beta_2$-microglobulin genes as isolated and characterized by Parnes and Seidman, *Cell*, 29:661–669, (1982), and Gusow et al., *J.Immunol.*, 139:3132–3138 (1987), respectively, are employed for homology.

Construction of Inactivation Vector 1

The inactivation vectors are constructed from 4kb HindIII fragment of the genomic DNA which encompasses the second, third and fourth exons of the $\beta_2$-microglobulin gene. The 4kb HindIII fragment subcloned into pBR322 is digested with EcoRI and the selectable neomycin phosphotransferase ($neo^R$) gene inserted. The $neo^R$ gene is obtained from pSV2neo (Southern and Berg, *Mol. Appl. Genet.*, 1:332, (1982)). The resulting vector is called B2KO1.

Construction of Inactivation Vector 2

The starting plasmid for the construction of the second vector is B2KO1. In this case, the herpes simplex virus type 1 thymidine kinase gene is inserted at the HindIII site of B2KO1.

Inactivation of One Copy of $\beta_2$-microglobulin

The DNA which is used for transformation in the first or second stage comprises the inserted sequence with flanking homologous sequences from the cloning plasmid B2KO1 and the same sequence flanked at one end by tk gene free of the bacterial plasmid DNA. The resulting DNA fragments are purified by ethanol precipitation and cleared by passage through a 0.22 micron filter. The DNA is isolated by conventional means and introduced into the keratinocyte cells by microinjection (Capecchi, *Cell*, 22:479–488 (1980). Approximately 5–50 copies of the DNA constructs are injected into each nucleus. The cells are then grown in selective medium comprising 200 µg/ml of G418 (Geneticin, Gibco Labs). For the second construct, the cells are also plated in Gancyclovir (Syntex Corp, Palo Alto, Calif.) or Ayclovir (Burrows-Wellcome, Research Triangle Park, N.C.). Cells from colonies are isolated and analyzed by the polymerase chain reaction and Southern blot hybridization. Cells demonstrating one copy of the $\beta_2$-microglobulin being inactivated are used for knocking out the second copy.

Inactivation of The Second Copy of the $\beta_2$-microglobulin Gene Gene

Cells obtained from above with a single inactivated $\beta_2$-microglobulin gene are microinjected as described above with the modified B2KO2 plasmid and cells resistant to Gancyclovir or Acyclovir isolated. Cells which lack Class I gene expression are isolated by combining the cells with monoclonal antibodies specific for $\beta_2$-microglobulin and complement as described by Parish et al., (1974), *Eur. J. Immunol.*, 4:808. Resulting viable cells are grown in selected medium and passed through an affinity column of the same monoclonal antibodies. The column is prepared as described by Harlow and Lane, (1988), *Antibodies: A Laboratory Manual*, CSH Press. Southern blot analysis of the cells is performed to establish the proper locus of integration. The cells are then expanded and stored for further use.

Generation of Monolayer of Keratinocytes

The resulting cells lacking Class I MHC are used to grow a monolayer of keratinocytes as described by Rheinwald and Green, *Cell* 6:331–343, (1975). This layer is transplanted onto allogenic mice as described by Rheinwald and Green, (1975), supra. The cells adhere to the surface and grow to provide a protective skin layer.

Following the same procedure as described above for $\beta_2$-microglobulin the HLA-DR genes may be inactivated by employing homologous sequences flanking the $\alpha$ or $\beta$-subunit of the HLA-DR gene of the host cell. In this way cells which have the Class II MHC antigen or may have the capability to have the expression of such antigen induced are prevented from expressing the primary Class II antigen associated with the cellular immune response.

In the next study, embryonic stem cells were modified by homologous recombination with one of the $\beta_2$-microglobulin genes.

II. Inactivation of $\beta_2$-microglobulin gene. Construction of the Targeting Plasmid The plasmid pKC$\beta_2$B contains the entire $\beta_2$-M gene within an 8.4 kbp XhoI fragment (Ozato and Orrison, *Proc. Natl. Acad. Sci. USA*, 82:2427–2431, (1985); Warner et al., *Bio. Reprod.*, 36:611–616, (1987). The 5'XhoI to BamHI fragment of this gene was subcloned into pUC19. Two KpnI restriction enzyme sites, one in the 5' flanking DNA and the other within the first intron, were removed by digestion with KpnI followed by treatment with T4 polymerase and re-ligation. A unique ClaI site was created in exon 2 by partial digestion with EcoRI followed by treatment with Klenow polymerase and ligation with ClaI linkers. The 1150 bp XhoI to HI fragment of the plasmid pMCl Neo (Kim and Smithies, *Nucleic Acid Res.*, 16:8887–8903, (1988)), containing a neomycin gene driven by the Herpes simplex virus thymidine kinase gene (HSV-tk) promoter and a polyoma enhancer, was inserted via linkers into this ClaI site. Two plasmids, C65.2.3 and C65.5.9, were obtained that differed in the transcriptional orientation of the inserted fragment with respect to that of the $\beta_2$-microglobulin gene. The 5' XhoI to KpnI fragment of each of these was cloned into pUCl9 in order to obtain the targeting vectors used in our experiments. In plasmid C84.4B the 5' to 3' orientation of the neomycin and $\beta_2$M promoters is identical. The opposite configuration occurs in plasmid C84.2D.

Culturing, Electroporation, and Selection of ES Cells

The ES cell line E14TG2a (Sawicki et al., *Nature*, 294:450–451, (1981)), was cultured on mitomycin treated primary embryonic fibroblast-feeder layers essentially as described (Ostrand-Rosenberg et al., *Proc. Natl. Acad. Sci.* 86:5084–5088, (1989)). The embryonic fibroblasts were prepared from embryos from C57BL/6 females that had mated 14 to 17 days earlier with a male homozygous for a neomycin transgene (Evans and Kaufman, *Nature*, 292:154–156, (1981)); these cells are capable of growth in media containing G418. Electroporation conditions were similar to those that have been described previously (Doetschman et al., *Nature*, 330:576–578, (1987)). ES cells were trypsinized, resuspended in culture media at a concentration of $4 \times 10^7$/ml and electroporated in the presence of the targeting DNA at a concentration of n in the first experiment and 5nM DNA in the second. A voltage of 300 V with a capacitance of 150–250 µF was found optimal with an electroporation cell of 5 mm length and 100 mm² cross section. $5 \times 10^6$ electroporated cells were plated onto mitomycin-treated fibroblasts in 100 mm dishes in the presence of Dulbecco's modified Eagle's media (DMEM) supplemented with 15% fetal bovine serum (FBS) and 0.1 mM 2-mercaptoethanol. The media was replaced 24 hr after electroporation with media containing 200 µg/ml G418.

Analysis of G418 Resistant ES Cell Colonies

ES colonies visible 10–14 days after electroporation were picked with drawn out capillary pipettes for analysis using the polymerase chain reaction (PCR). Half of each picked colony was saved in 24-well plates already seeded with mitomycin-treated feeder cells. The other halves, combined in pools of 3–4, were transferred to Eppendorf tubes containing approximately 0.5 ml of PBS and analyzed for homologous recombination by PCR. Conditions for PCR reactions were essentially as described (Linney and Donerly, Cell, 35:693–699, (1983)). The ES cells were pelleted, resuspended in 5 μl of phosphate buffered saline (PBS), and lysed by the addition of 55 μl of H20 to each tube. DNAses were inactivated by heating each tube at 95° C. for 10 min. After treatment with proteinase K at 55° C. for 30 rain, 30 μl of each lysate was transferred to a tube containing 20 μl of a reaction mixture including PCR buffer, 1.5 μg of each primer, 3U of Taq polymerase, 10% DMSO, and dATP, dCTP, dGTP and dTTP each at 0.2 mM. PCR was carried out for 55 cycles using a thermocycler modelled after one described previously (Kim and Smithies, supra, (1988)), with 65 seconds melt at 920° C. and a 10 min annealing and extension time at 65° C. The two priming oligonucleotides, TGGCGGACCGCTATAGGAC and GATGCTGATCA-CATGTCTCG, correspond respectively to sequences located 650 bases 3' of the start codon of the neomycin gene and sequences located in exon 3 of the $\beta_2$-m gene. 20 μl of the reaction mix was electrophoresed on agarose gels and transferred to nylon membranes (Zeta Bind). Filters were probed with 32P-labelled 450 bp EcoRI to KpnI fragment of the $\beta_2$-M gene.

Preparation and Restriction Enzyme Analysis of Genomic DNA

Genomic DNA was prepared from ES cells, whole new born mice, and mouse tails lo by conventional methods. DNA was digested with restriction enzymes as directed by the manufacturers and fragments were separated on 0.7% agarose gels. DNA was transferred to nylon membranes and probed with the 32P labelled fragment described above.

Embryo Manipulation and Blastocyst Injection

Mice were purchased from either Jackson Laboratories (Bar Harbor, ME) or Charles River (Raleigh, N.C.). C57BL/6 blastocysts were obtained from 3 to 4 week old superovulated females. Uteri were flushed with M2 media (Joyner et al., *Nature*, 338: 153–156, (1989)), 3.5 days after ovulation. Blastocysts were collected, washed several times in fresh M2 media, and placed in a 100 μl droplet of M2 under paraffin oil. ES cells were trypsinized, washed once with fresh DMEM media and diluted to approximately $2\times10^6$ cell/ml. 5 μl of cells were added to the droplet containing the blastocysts. 10 to 15 ES cells were injected into the blastocoel of each blastocyst. Following injection 6 to 9 blastocyst were returned to each uterine horn of pseudopregnant females mated 2.5 days previously with vasectomized males. Both C57BL/6×DBA Fl and C57BL/6×CBA Fl mice proved to be excellent foster mothers, yielding a pregnancy rate close to 100% and able to raise small litters.

Isolation and Characterization of Targeted ES cells

Two independent targeting experiments were carried out. In each, $2\times10^7$ cells were electroporated in the presence of the incoming DNA, and were then cultured in media containing G418. After about two weeks, G418 resistant colonies were readily apparent. A portion of each colony was then transferred to an individual well of a 24-well plate, while the remaining portion was pooled with portions from two to four other colonies for PCR analysis. In the first experiment, one pool gave a positive PCR signal out of 32 pools that included a total of 100 G418 resistant colonies. The three individual colonies that had contributed to this positive pool were analyzed individually by PCR, and a positive clone, ES39B, was identified. Similar analysis of 134 G418 resistant colonies obtained in the second experiment also yielded a clone, ES22A, which generated the 910 bp DNA fragment indicating successful targeting when subjected to PCR.

In order to verify the targeted disruption of one copy of the $\beta_2$-M gene, (the gene is autosomal and present in two copies), the two PCR positive clones, ES39B and ES22A, were expanded, and their DNA was isolated and then analyzed by Southern blotting using a probe that detects sequences from the second exon and part of the first intron of the $\beta_2$-M gene. Patterns obtained with the restriction enzymes XbaI, BamHI and KpnI match those expected if one of the two copies of the $\beta_2$-M gene had been disrupted in the planned manner in the PCR-positive clones. That is, one DNA fragment identical in size to that present in untreated cells, was present with all three enzymes. An additional fragment of the size predicted for a homologous recombination event was present only in the PCR-positive clones. The insertion of the neomycin gene into the second exon by recombination results in an XbaI fragment detectable with the $\beta_2$-M specific probe that is approximately 1 kb longer than the equivalent fragment in the native locus. A new BamHI site is introduced into the locus by the targeting DNA, reducing the size of the BamHI fragment detected by the β-m probe from 10.6 kbp to 900 bp. A new fragment is also seen after KpnI digestion. In ES39B the KpnI fragment is 7 kb in length, as predicted by a crossover between the 5' end of the targeting plasmid and the native locus. In ES22A this new KpnI fragment is 4.0 kb in length, which indicates that the deleted KpnI sites were not incorporated into the locus. This observation indicates that one of the, crossovers in cell line ES22A resolved between the third KpnI site of the native locus and the inserted neomycin gene of the incoming DNA, presumably after branch migration of a crossover intermediate. Although the 5' crossover sites differ, both modified cell lines now contain a $\beta_2$-M gene disrupted in the planned way by insertion of a neomycin gene in exon 2. Re-hybridization of the filter used for the autoradiography with a probe for the neomycin gene shows that the only bands that hybridize are those predicted by time structure of the construct.

Chimeric Offspring of Targeted ES Cells

The two ES cell lines carrying the inactivated $\beta_2$-M genes are expected to allow the introduction of this mutation into the mouse germline. Toward this end, we injected 10 to 15 cells into C57BL/6 blastocysts. Embryos were reimplanted into pseudopregnant females. Because the ES cell line E14TG2a was isolated from strain 129/01a embryos, it and all cell lines derived from it are expected to carry the coat color markers characteristic of this mouse strain. These include the dominant $A^w$ allele at the agouti locus, the recessive chinchilla allele at the c-locus, and the recessive p-allele (pink-eyed dilution) at the p-locus (Quinn et al., *J. Reprod. Fertil.*, 66:161–168, (1981)). Contribution of ES cells to the mesoderm-derived portions of hair follicles results in an agouti coat. Hair follicles to which melanocytes of ES cell origin (and therefore carrying the p and cch mutations) have migrated produce cream-colored hairs. Both of these coat colors are easily distinguished from the solid black coat seen in pups derived from nonagouti C57BL/6 host blastocysts.

More than 70% of surviving pups are chimeras. The intensity of the 6.1 XbaI band diagnostic of the targeted $\beta_2$-M locus shows that the modified ES cells contributed extensively to the tissue of this animal.

Generation of Chimeric Mice

Three to four week old C57BL/6 female mice were superovulated by the sequential injection of PMS and hCG and mated with fertile males of similar strain. Four days after mating, the female mice were sacrificed, and blastocysts obtained by flushing the uterus with M9 media. The collected blastocysts were transferred to a droplet of the same media that was submerged in paraffin oil and also contained some ES22a cells. These cells had been prepared for injection by trypsinization followed by washing and resuspending in M2 media. Ten to fifteen ES22a cells were introduced into the blastocoel of each blastocyst using standard micromanipulation techniques. The ES cell containing blastocysts were then transferred to the uterus of a pseudopregnant foster mother. Foster mothers were obtained by mating B6/D2 females with vasectomized male mice. Females which had mated 2.5 days prior to the date of transfer, as asserted by the presence of a vaginal plug were used as foster mothers for the ES cell containing blastocysts. Development of the blastocysts continues in vivo and pups were generally born 16–18 days later. The contribution of the ES cells to the offspring could be judged visually by examination of the coat color of the pups. The blastocysts were obtained from C57BL/6 mice, which are solid black in color. The ES cell line E14TG2a, the parental line from which ES22a was derived was isolated from 129/Ola mice. This mouse strain is cream in color, the combined effect of three coat color genes, the dominant $A^w$ allele at the agouti locus, recessive pink-eyed-dilute allele at the p locus and the recessive $c^{ch}$ at the C locus. Offspring in which the ES22a had participated in the formation of the animal had coats containing brown and cream hairs. About 80% of the pups from blastocysts containing ES22a cells showed some degree of coat color chimerism.

Generation of Animals Heterozygous for the Mutated $\beta_2$-M Gene.

If ES22a cells contribute to the gonads the animals would be expected to generate sperm which contain the ES22a genome and pass it on to its offspring. The ES22a genome is homozygous for the dominant color coat marker $A^w$. If the chimera is mated with an animal that is non-agouti such as a C57BL/6 or B6/D2, offspring that arise from sperm or ES cell origin can be distinguished from those derived from sperm or blastocyst origin by their coat color. 50% of these agouti animals would be expected to inherit the mutated $\beta_2$-M gene. These can be identified by analysis of DNA isolated from the tails. 1 cm of tail was therefore removed from the agouti animals, and DNA prepared by standard techniques. DNA was digested with either the restriction enzyme XbaI or HindIII and analyzed by Southern blotting and probing with a radioactively labelled fragment of the $\beta_2$-M gene. The presence of an XbaI or HindIII fragment 1Kb larger than that found in control mice is indicative of the presence of the mutated $\beta_2$-M gene in the animal.

Generation of Animals Homozygous for the Mutated $\beta_2$-M Gene.

Male and female animals whose DNA indicated that they were carrying one copy of the mutated $\beta_2$-M gene were mated. Offspring of these matings were again analyzed for the presence of the larger XbaI or HindIII fragments. As expected one quarter of the offspring from such matings were homozygous for the defective gene. These animals now represent a new mouse strain which carries the mutation that was originally introduced by homologous recombination into the ES cell E14TG2a.

Determination of the Phenotype of the $\beta_1 M$ –/– Mice

To determine whether as expected, the mutation of the $\beta_2$-M protein resulted in loss of class I expression, two animals homozygous for the $\beta_2$-M mutation were sacrificed and examined for the presence of cell surface class I expression. Cells isolated from lymph node, spleen and thymus were examined with monoclonal antibodies directed against the Class I antigens H-2$K^b$ and H-2$D^b$. Both 129/Ola, the mouse strain frown which the ES cell line was derived and C57BL/6 the strain with which the chimera giving rise to these animals had been mated, express the H-2b haplotype. No staining above background was seen with cells obtained from the homozygous $\beta_2$-M –/– mice in any of the tissues examined. Therefore, as predicted, the inactivation of $\beta_2$-M gene resulted in an animal that fails to express Class I antigens at the cell surface. The animals appeared healthy and could not be distinguished visibly from their litter mates.

The effect of lack of class I antigens on the maturation of T-cells was examined by isolating and staining thymocytes with antibodies that delineate various stages of T-cell differentiation. The data showed that the CD4$^-$8+, CD4$^-$8+, and CD4$^-$8+, cell populations in the thymuses of normal, $\beta_2$-M –/–, and heterozygous animals are identical. In contrast, the CD4$^-$8$^+$ populations differ between animals of the different genotypes. CD4$^-$8$^+$ cells represent 10% of the cells of the normal thymus but less than 1% of the cells in the thymus of the $\beta_2$-m mice. Interestingly, the number of these cells in the heterozygote is also somewhat reduced.

To determine whether the absence of the Class I genes affected the maturation of T-cells as indicated by the expression of the T cell receptor genes, thymocytes were stained with antibodies directed against either TCR$\alpha\beta$ or TCR$\gamma\delta$ receptor. No significant difference in the profile of $\alpha\beta$ cell receptor positive cells was seen in $\beta_2$-M –/– animals compared to normal, indicating that Class I antigens are not needed for the maturation of thymocytes to TCR bearing CD4$^+$8$^+$, or CD4$^+$8$^-$ cells.

Next, peripheral T-cells were examined for expression of $\alpha\beta$ TCR and CD4 and CD8. The yields of T-cells bearing $\alpha\beta$ TCRs from the spleen and lymph nodes of animals lacking $\beta_2$-M were not significantly different from those of normal littermate controls. Between 20% and 32% of all T-cells bearing $\alpha\beta$ TCRs also bore CD8 in $\beta_2$-M +/+ and +/– animals. Although CD4$^-$, CD8$^+$ thymocytes were somewhat depleted in $\beta_2$-M heterozygous animals, the level of peripheral CD8$^+$ T-cells in these mice were comparable to those of normal littermates. By contrast, virtually none of the $\alpha\beta$ TCR-bearing T-cells expressed CD8 in animals homozygous for the $\beta_2$-M mutation. A preliminary experiment was done to find out whether the few $\alpha\beta$ T-cells which appeared CD8$^+$ in mutant mice were due to noise in the staining procedures. T-cells from these animals were therefore grown for several days on plastic coated with anti-CD3 antibody and in interleukin-2, a procedure which often stimulates the proliferation of CD8$^+$ T-cells preferentially. CD8 bearing $\alpha\beta$+ T-cells did not appear in greater numbers after such treatment, although $\gamma\delta$ bearing T cells did grow out. The conclusion is that CD8$^+$, $\alpha\beta$ cells are virtually absent in animals which lack Class I MHC expression.

Thymocytes and T-cells from spleen and lymph node were also examined for expression of $\gamma\delta$ TCRs. The numbers of these cells were similar in $\beta_2$-M –/– mice and controls. An outgrowth experiment (described above) showed that the $\gamma\delta$-bearing cells from $\beta_2$-M could proliferate and, moreover, preliminary examination of these cells indicated that about a quarter of them bore CD8. Therefore these studies indicate that $\gamma\delta$ T-cells may not require Class I expression for their existence, even if they also bear CD8.

III. Transplantation of MHC-deficient skin cells. Generation of Mice

Mice lacking a functional $\beta_2$-microglobulin gene were derived as described above, using homologous recombination to specifically disrupt this gene in ES cells, using the 129 strain of mice. These modified cells were used to generate chimeric mice, which were bred to C57BL/6 mice. Pups carrying the disrupted copy of the $\beta_2$-microglobulin gene were intercrossed to produce founder H-2$^b$ $\beta_2$-microglobulin deficient homozygotes. This procedure generated mice with a mixed genetic background, possessing minor histocompatibility antigens from both the C57BL/6 and 129 strains, but lacking a functional $\beta_2$-microglobulin locus. Table 1 shows the MHC haplotypes of the various mouse strains which were used in these experiments.

TABLE 1

| Strain | K | IA | IE | D | L |
| --- | --- | --- | --- | --- | --- |
| C57B1/6 | b | b | — | b | — |
| 129 | b | b | — | b | — |
| B10-D2(R107) | b | b | — | d | d |
| B10-BR | k | k | k | k | — |
| B10-A(2R) | k | k | k | b | — |
| CBA | k | k | k | k | — |

Grafts onto Syngeneic Recipients

Skin grafts were performed according to an adaptation of the method of Billingham and Medawar (1951) *J. Exp. Bio.* 28:385. Full thickness skin derived from the trunk of a donor mouse, 6–10 weeks old, was fitted onto a graftbed on the flank of the recipient mouse, 8–12 weeks old. The site was covered with a petroleum gauze patch, and a plaster bandage was wrapped around the recipient's midsection. The bandage was removed on day 7, and the grafted tissue was observed visually each day thereafter. The experiments were carried out using a blinded format.

Skin grafts from mice deficient in $\beta_2$-microglobulin were readily accepted by syngeneic recipients, while control allogeneic grafts onto these same recipients were rejected in a normal time course. In contrast, bone marrow transplants from these same animals were rejected by syngeneic recipients by an NK-cell mediated process. The data from the skin graft experiments is shown in Table 2.

TABLE 2

| | DAYS GRAFT SURVIVAL Donor | |
| --- | --- | --- |
| Recipient | 129 | H-2$^b$ $\beta_2^-$ |
| (C57BL/6 × 129)F$_1$ | >300 days | >300 days |
| C57BL/6 | 13.8 ± 2.2 | 13.9 ± 2.2 |
| B10.D2(R107) | 11 | 11.3 ± 0.5 |
| B10.BR | 11 | 11.7 ± 1.0 |
| B10.A(2R) | 11.3 ± 0.6 | 11.9 ± 1.2 |

It can be seen from the above data that lack of MHC Class I antigens does not affect the rejection of a skin graft from a syngeneic donor, shown by the data from the (C57BL/6× 129)F$_1$ recipient. The H-2$^b$ $\beta_2$-cells expressed minor histocompatibility antigens from the 129 parent, and so the grafts were rejected by the C57BL/6 homozygous mice. The length of time before the graft was rejected was longer for minor histocompatibility antigen mismatches (13.9 days) than for grafts across a Class I mismatch (11.3–11.9 days).

Skin grafts onto H-2 Class I mismatched recipients

To test the transplantability of the $\beta_2$-microglobulin deficient tissue in the presence of a Class I MHC antigen mismatch, the breeding of several new mouse strains was required.

To produce F1 recipient animals, B10 congenic strains were crossed with the 129 strain. The minor antigen profiles of B10 and C57BL/6 are virtually identical, and so (B10× 129)F$_1$ mice are tolerant to the minor antigens which are present in the H-2$^b$ $\beta_2$-microglobulin deficient mice.

To create a donor strain carrying a Class I MHC mismatch, the $\beta_2$-microglobulin deficiency was bred into a B10 strain, B11.BR, which has the H-2$^k$ haplotype. Mice were derived which had the MHC phenotype H-2$^{k/k}$, $\beta_2$-microglobulin$^{-/-}$. These mice carried minor histocompatibility antigens from both the B10 and the 129 strains.

Whole skin from these animals was transplanted by the method described above, onto (B10.A(2R)×129)F$_1$ recipients. The recipient mice are H-2D$^{b/b}$, while the donor mice, as noted above, are H-2D$^{k/k}$. Therefore the MHC Class I alleles are mismatched at the D locus. However, since the donor mice lack $\beta_2$-microglobulin, the MHC Class I antigens are not expressed on the cell surface, and so the grafts were not rejected by the mismatched recipient. Table 3 shows the survival time of skin grafts using these animals.

TABLE 3

| | DAYS GRAFT SURVIVAL Donor | |
| --- | --- | --- |
| Recipient | B10.BR | H-2$^k$ $\beta_2^-$ |
| (B10.A(2R) × 129)F$_1$ | 12 days | >90 days |
| B10.BR | >90 days | 12 days |
| (B10.BR × 129)F$_1$ | >90 days | >90 days |

These results show that a homozygous mutation at the $\beta_2$-microglobulin locus effectively eliminated the ability of the D$^k$ Class I MHC antigen to act as a major transplantation barrier. The recipient mice were still able to reject the $\beta_2$-microglobulin deficient cells when there was sufficient mismatch at minor histocompatibility loci, as shown by the ability of B10.BR recipients to reject the skin grafts.

In vivo, Class I MHC molecules serve the role of presenting foreign peptide antigens for recognition by CD8$^+$ T cells. As a result, CD8$^+$ T cells are able to recognize and reject transplanted tissue solely on the basis of its expression of foreign MHC Class I antigens. The prolonged survival of MHC Class I mismatched, $\beta_2$-microglobulin deficient skin grafts indicates that CD8$^+$cells are made of the recipient's this tissue as foreign, allowing these cells to avoid an entire branch of the recipient's immune response.

IV. Targeting in Human Somatic RPE Cells

The HPRT gene in human retinal pigmented epithelial (RPE) cells was targeted using homologous recombination to demonstrate the ability to achieve a precise alteration in nontransformed, diploid somatic human cells prior to targeting genes associated with MHC antigen expression.

A fragment of the human HPRT gene sequence (Edwards et al., *Genomics* 6:593–608 (1990)) ("R1" 11777–17810 ) subcloned from lambda clone Huλ3 (ATCC) (Patel et al., *Molec. and Cell. Biol.* 6(2):393–403 (1986)) was subcloned into a pUC cloning vector using standard procedures. The neo$^r$ gene from the vector pMC1neo (Thomas and Capecchi, *Cell* 51:503–512 (1987)) was inserted into the unique XhoI site located in exon 3 of the hHPRT gene. This vector, named HPRT.MC1neo.ro (FIG. 1), contains 6 Kb of homology to the hHPRT locus, and was cut with either BglII or Hind III to create insertion vector and replacement vector substrates, respectively. The vector substrates were purified by standard methods and the DNA concentration was adjusted to 1 mg/ml. 1 μg of linear vector DNA was electroporated into each sample of normal male, primary, human RPE cells (4×10$^6$ cells/sample) isolated from eye tissue from human cadavers using the procedure of Mayerson et al. (*Invest. Opthalmol. & Visual Sci.* 26:1599–1609 (1985)). The cells were then plated into non-selective growth media onto three 150 mm tissue culture dishes and incubated at 37° C. for two days. On the third day the growth media was changed and media containing 150 µg/ml of G418 was added. The growth media was changed again on day 5 and media containing 150 µg/ml G418(neo) and 400/µg/ml 6-thioguanine was added. This media was changed every third day thereafter. Approximately two weeks after transfection, growing colonies derived from cells in which the targeting vector had homologously recombined with the cell's sole HPRT gene were evident on about one in ten plates. No colonies were evident on any plates unless vector DNA was included. Individual clones (colonies) were grown to mass culture on 150 mm dishes. Samples of each clone were lysed in a detergent-containing buffer and high molecular weight (HMW) DNA was isolated by standard procedures. These samples were digested with BamHI and 10 µg aliquots were analyzed on a Southern blot using a probe cloned by PCR from the hHPRT gene (3' of the HPRT R1 vector sequences). The probe was prepared using the following primers:

PC 5: 5' GACTCAGAATTCGCATGCTTAATTAA-GATTGATTGATTGA-TGGTTTACAGTAGGAC 3'

PC 31: 5' GATTACGAATTCAAGCTTGTCAAAG-CATTTTCTACCACTGA-GAATTGATC 3'.

Figure 2:
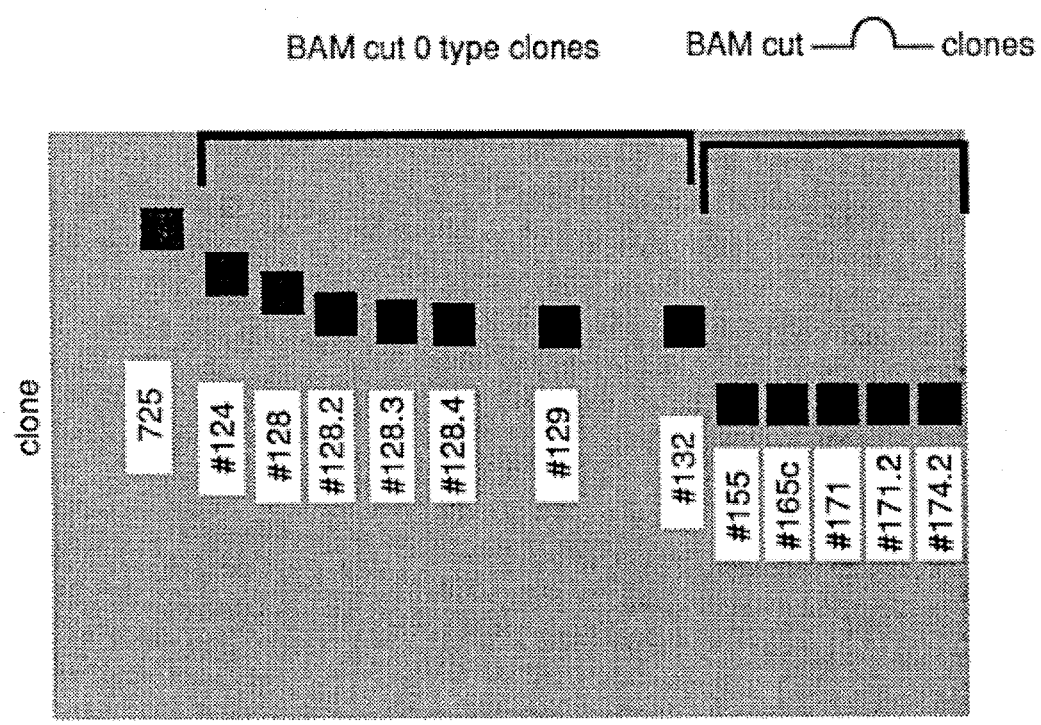
FIG. 2 is a Southern blot of HPRT-targeted insertional (O-vector) and replacement (omega "Ω" vector) recombinant clones, as described in Example IV, infra.

These blots showed a 20 Kb band in the case of wild-type, parental DNA, a 15 Kb band in the clones transfected with the BglII-cut vector and selected with G418 and 6-thioguanine; and a 6 Kb band in the cells transfected with the HindII-cut vector and selected in G418 and 6-thioguanine (FIG. 2). At least three additional digests were used to analyze each of these clones. All indicated that each selected (G418+6-thioguanine) clone had undergone an accurate replacement (HindIII) or insertion (BglII) recombination reaction. Both insertional and replacement recombination events occurred with a frequency of approximately $10^{-7}$ recombinants/input cell. These data are summarized in Table 4. Only one clone was counted per transfection to ensure the independence of each recombinant clone. Intramolecular recombination was studied in this system by examining the reversion frequency of several of the insertional mutants. All of these mutants reverted to an HPRT+, neo$^s$ phenotype at an equivalent rate. These revertants were detected at a frequency of $10^{-5}$ per input cell. Many of these clones were shown to be true recombinants by Southern blotting. These results demonstrate gene targeting in the human primary RPE cells to inactivate the HPRT gene.

from the 5' to 3' termini: a 7.6 Kb fragment of genomic DNA homology (NotI-MluI fragment from the region upstream of exon 1 of the $\beta_2$-M gene); a fully functional neomycin (Neo) resistance gene (derived from pMC1Neo) for selecting cells which stably integrate the vector, a downstream homology or DSH fragment (a 1.4 Kb XbaI-SmaI fragment from downstream of exon 4 of the $\beta_2$-M gene); a Herpes thymidine kinase gene (2.0 Kb); the 5' end of the recombinant locus including a strong CMV early promoter and enhancer; a partial cDNA sequence (603 bp) for human CD4 (T4) (Maddon et al., Cell 42:93–104 (1985); GENBANK: HUMATCT4) comprising part of the 5' untranslated region, the signal sequence (amino acids nos. 1–23) and first two immunoglobulin-like domains of the mature human CD4 gene product (amino acids nos. 24–222) fused inframe to the last 10 basepairs from exon 1 of the $\beta_2$-M gene (encoding an alanine, then the first two codons of the mature $\beta_2$-M gene product); and a 3.5 kb fragment from the, first intron of the $\beta_2$-M gene (up to the ClaI site) (FIG. 3A). The human $\beta_2$-M locus is shown in FIG. 3B, and the correctly targeted recombinant locus is shown in FIG. 3C.

Figure 4:
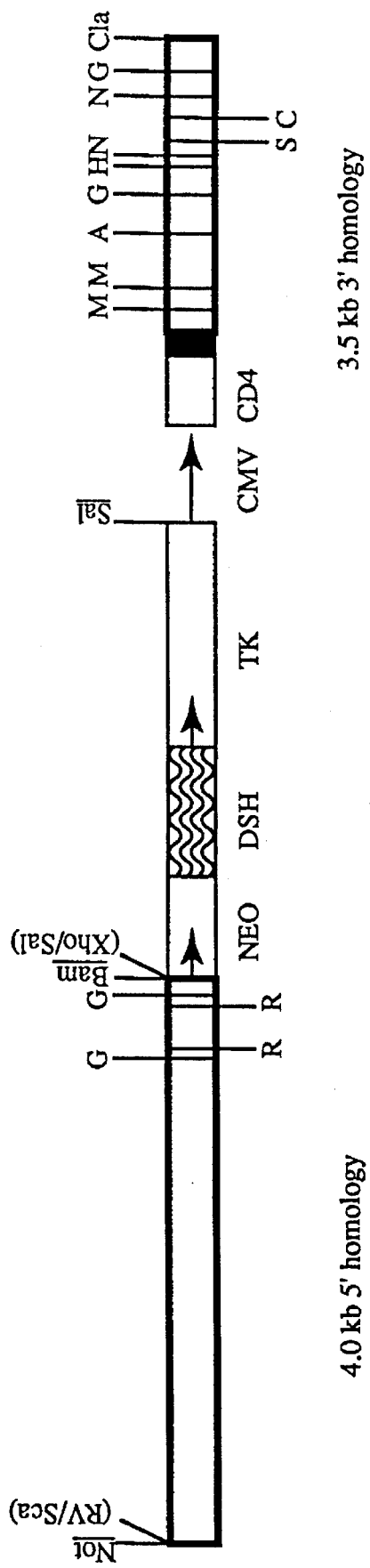
FIG. 4 is a diagram of the #148β$_2$-M targeting vector, described in Example V, infra.

An additional targeting vector, designated #148 (FIG. 4), was constructed by removing 3.6 Kb of the 5' region upstream of the $\beta_2$-M promoter leaving 4.0 Kb of homology.

An ELISA was developed to detect the chimeric CD4-$\beta_2$-M gene product that would be produced by a homologous targeting event by binding proteins containing a $\beta_2$-M encoded epitope to the surface of a microtiter well and detecting bound proteins possessing a CD4-encoded epitope. Microtiter plates were coated with a rabbit antihuman $\beta_2$-M IgG preparation (DAKO Corp., Carpinteria, Calif.). Nonspecific binding sites were saturated with ovalbumin. The sample was applied and incubated. After washing, a murine monoclonal anti-human CD4 antibody (Ortho Diagnostic Systems, Raritan, N.J.) known to bind an epitope contained in the portion of CD4 used for the inactivation construct was added to the wells and incubated. In the next step, an alkaline phosphatase-conjugated rabbit anti-mouse IgG2a (Cappel, Organon Teknika, Corp., Durham, N.C.) was incubated in the wells. Subsequently, the wells were incubated with the phosphatase chromogenic substrate p-nitrophenyl phosphate, and the results were read on a plate reader. To allow formulation of the ELISA assay, RPE cells were harvested from a passage 6 culture and transfected with control vectors: either a full length CD4 expression vector

TABLE 4

| | RPE/HPRT Targeting Results | | | |
|---|---|---|---|---|
| DNA | TYPE | NEO$^r$ FREQ. | RECOMB. FREQ. | RATIO |
| BglII HPRT MC/RO | O vector | — | $1.3 \times 10^{-7}$ | — |
| HindIII HPRT MC/RO | Ω vector | — | $7.8 \times 10^{-8}$ | — |
| BglII HPRT MC/RO | O vector | $1.4 \times 10^{-5}$ | $3.8 \times 10^{-7}$ | 36:1 |
| HindIII HPRT MC/RO | Ω vector | $1.1 \times 10^{-5}$ | $1.3 \times 10^{-7}$ | 85:1 |
| BglII 86.8 | O vector | $2.0 \times 10^{-6}$ | $2.0 \times 10^{-7}$ | 10:1 |

V. Targeting of the $\beta_2$-microglobulin locus in Human Cells

These experiments demonstrate the targeting of loci for decreasing the cell-surface expression of Class I MHC antigens in normal, diploid human cells by inactivating the $\beta_2$-microglobulin ($\beta_2$-M) gene in normal, diploid human RPE cells.

Two approaches were developed for inactivating the $\beta_2$-M locus to decrease Class I MHC antigen expression. In the first approach, a targeting vector designated #137 was constructed with the following elements described proceeding containing the CMV immediate-early promoter, intron, the CD4 signal sequence, and the full-length CD4 cDNA coding region and SV40 polyadenylation signal, or a$\beta_2$-M fusion protein expression vector, containing the CMV promoter, and a chimeric cDNA consisting of the CD4 signal sequence and the first two immunoglobulin-like epitopes of CD4 fused to the full length mature coding region of $\beta_2$-M, and the SV40 polyadenylation signal, by electroporation (0.5 ml cells; 270 volts, 960 µF, $8 \times 10^6$ cells/ml in DME/F 12 media without serum, 1–5 µg linear DNA at room temperature).

One day post-transfection, conditioned media was harvested from the transfected cells and tested in the ELISA which traps proteins containing a $\beta_2$-M encoded epitope and detects bound proteins possessing a CD4 encoded epitope. The resulting assay was shown to be specific for the CD4-$\beta_2$M fusion protein allowing detection of as few as 1000 expressing cells as tested by cell counting and sample dilution.

The #137 and #148 targeting vectors were linearized with restriction enzymes (as shown in Table 5) and transfected into RPE cells (passage 7–18) via electroporation, using from 2.0 to 7.5 μg vector per 4×10$^6$ cells. The cells were then plated in 12-well or 24-well plates. The day following transfection, G418 was added to the medium at a concentration of 400 μg/ml, and the cells were selected in G418 for approximately two weeks until G418-resistant colonies were apparent. Conditioned media from wells containing 1–10 colonies was screened using the ELISA to detect the chimeric CD4-$\beta_2$M gene fusion protein expected from correctly targeted clones. Conditioned media obtained from individual clones derived from each positive pool were rescreened and recombinant clones were identified. The data from nine independent targeting experiments is summarized in Table 5. Several ELISA positive clones were chosen at random for further analysis. These clones were expanded and assayed by Southern blot and radio-immunoprecipitation.

TABLE 5

RPE/$\beta_2$M Targeting Results

| DNA | Recombinants | Recombination Efficiency |
| --- | --- | --- |
| 2 μg Not I #137 | 12 | 6.4 × 10$^{-7}$ |
| 4 μg Not I #137 | 8 | 2.7 × 10$^{-7}$ |
| 4 μg Not I #137 | 3 | 3.8 × 10$^{-7}$ |
| 2 μg Not I #137 | 20 | 6.7 × 10$^{-7}$ |
| 4 μg Not I #137 | 3 | 1.0 × 10$^{-7}$ |
| 7.5 μg Not I #137 | 14 | 1.2 × 10$^{-6}$ |
| 2 μg Not I #137 | 16 | 2.5 × 10$^{-7}$ |
| 2 μg Xho I #137 | 35 | 6.4 × 10$^{-7}$ |
| 2 μg Not-Cla #148 | 30 | 7.5 × 10$^{-6}$ |

Figure 5A:
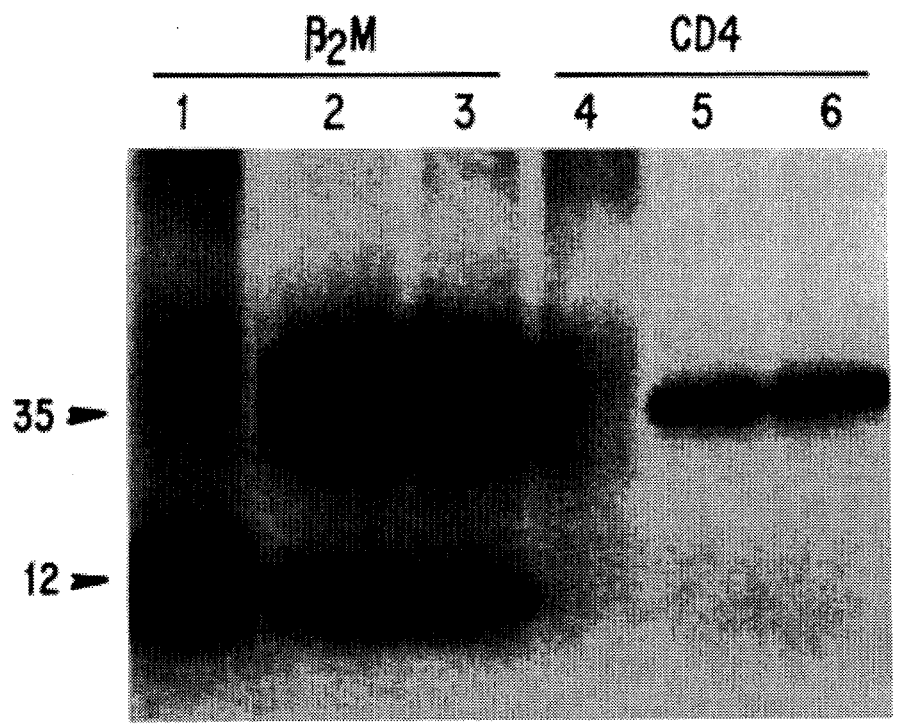
FIG. 5A–B is a SDS-PAGE gel showing the results of a radio-immunoprecipitation assay to detect secreted CD4-β$_2$-M fusion protein (FIG. 5A), and Southern blot analysis of ELISA positive β$_2$-M targeted clones (FIG. 5B), as described in Example V, infra.

A radio-immunoprecipitation (RIP) assay to detect the secreted fusion protein was performed as follows. A small subculture of untransfected and ELISA positive cells of each selected clone (clones: 24.1.3.2 and 28.1.6.2) was radiolabelled with S$^{35}$-methionine and S$^{35}$-cysteine for four (4) hours. Following this labeling period both cells and their supernatants were harvested. The cells were lysed, and the lysates and supernatants were incubated with either a rabbit anti-human$\beta_2$-microglobulin IgG preparation (DAKO, Carpinteria, Calif.) or a rabbit anti-CD4 IgG preparation (American BioTechnologies, Inc., Cambridge, Mass.). Subsequently, the samples were incubated with fixed *Staphylococcus aureus* cells which bind rabbit IgGs via Protein A on their surface. The resulting immune complexes were collected by centrifugation and electrophoresed on SDS polyacrylamide gradient gels. The gels were treated with sodium salicylate, a scintillant that increases the sensitivity of detection of the weak β particles emitted by $^{35}$S. The gels were then exposed to X-ray Kodak XAR-5 film and a fluorographic image was obtained (FIG. 5A).

The parental RPE cells (725, lanes 1,4 in FIG. 5A) show a 12 Kd band with the $\beta_2$M IP and no clear bands with the CD4 IP. In contrast, the two ELISA positive transfectants (lanes 2,3 and 5,6) show an additional 31 Kd band which was also present when they were immunoprecipitated with a CD4-specific antibody. This is the expected molecular weight of the CD4-$\beta_2$M fusion protein. Each of the ELISA positive clones also showed expression of the unmodified $\beta_2$M protein. This is the expected phenotype of clones modified at one copy of a diploid locus.

Figure 5B:
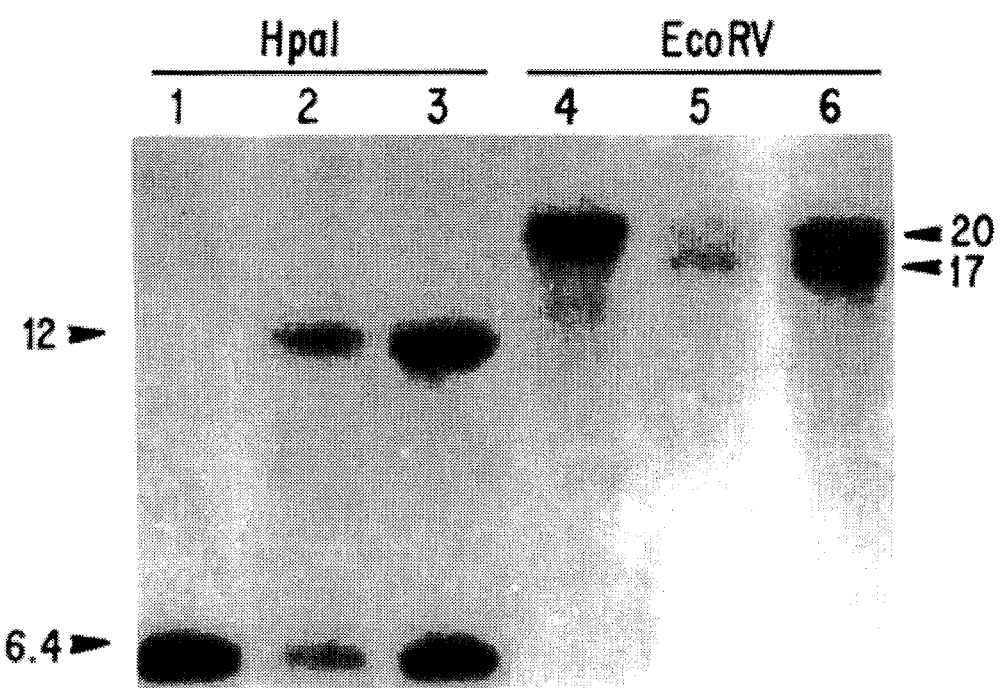

Additional ELISA-positive clones were expanded (clones 28.2.6.1 and 33.1.4.6) and genomic DNA was extracted for Southern analysis. Genomic DNA was digested with either HpaI or EcoRV, fractionated on a 1% agarose gel, blotted to a solid support and hybridized with a probe which flanks the 3' region of homology. Results are shown in FIG. 5B. The parental RPE cells show a single band with each digest (approximately 6.4 Kb in the HpaI digest and approximately 20 Kb in the EcoRV digest), whereas the ELISA positive clones show both the wild-type restriction fragment as well as a new recombinant band of the size expected for an accurate targeting event (approximately 12.5 Kb in the Hpa I digest and approximately 17 Kb in the EcoRV digest). This demonstrates the recombinant nature of these cells and demonstrates that this methodology permitted a determination of the frequency of the homologous recombination event and demonstrated the ability to target a locus directly related to MHC expression in a non-transformed, diploid human cell.

In certain cases, it may be desirable to eliminate the CD4 encoded portion of the fusion gene because of potential immunogenicity of the fusion peptide in a host organism into which it is introduced. In such cases gancyclovir is applied after targeting to select for surviving cells containing a deletion of DNA sequences between the DSH regions of homology (FIG. 3) eliminating the CD4 portion of the fusion protein. Alternatively, to eliminate secretion of the fusion protein from the cell, the signal sequence for CD4 may be deleted from the targeting vector and cell lysates screened for recombinants using the ELISA.

VI. Targeting with Neo Replacement Vectors

Figure 6:
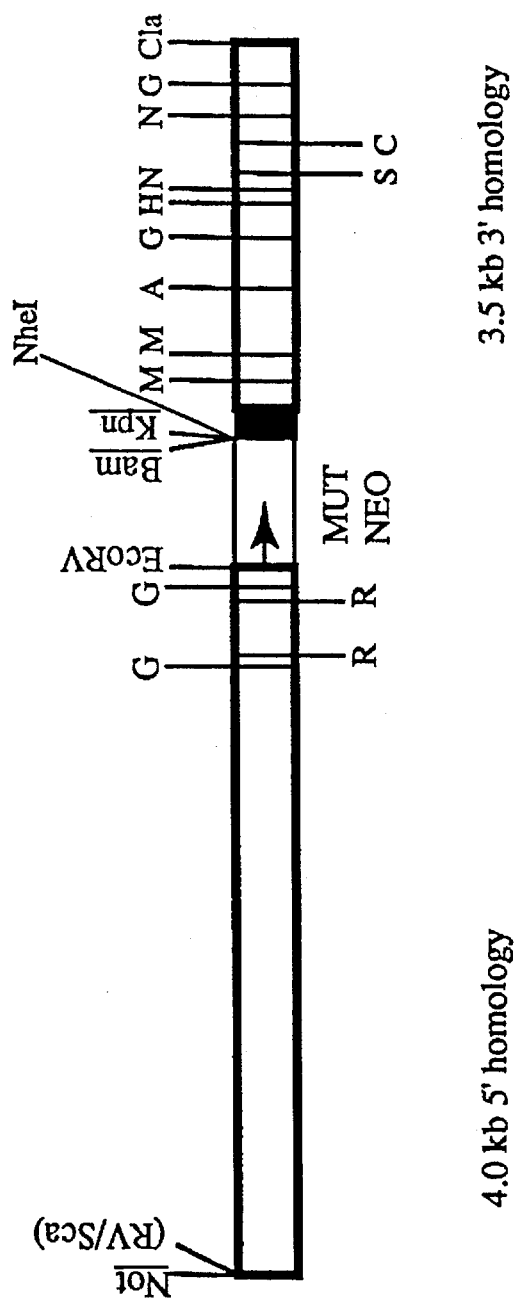
FIG. 6 is a diagram of the #159 Neo replacement targeting vector, described in Example VI, infra.

In a second approach, the #137 and #148 targeting vectors were replaced with a targeting vector designated #159 (see FIG. 6). This vector is a Neo replacement vectors. Vector #159 contains the same upstream homology region as p148, namely the 4.0 Kb ScaI-MluI fragment from the region upstream of exon I of the $\beta_2$-M gene, a mutant Neo expression unit (missing a XhoII restriction site at bp 1286 in the wildtype Neo DNA sequence) from pMC1Neo-mutant and a 3.5 Kb downstream homology region from an engineered NheI site 14 bp from the 3' end of exon 1 to the ClaI site in the first intron of the $\beta_2$-M gene. Successful targeting using this vector results in introduction of a null mutation at the $\beta_2$-M locus.

Normal human keratinocytes isolated from human foreskins and grown in the presence of mouse embryo fibroblast feeder cells are transfected by electroporation as described above using p159 which has been digested with with restriction enzymes NotI and/or ClaI using 2 μg of DNA per 4×10$^6$ cells. The cells are then plated in 100 mm or 150 mm tissue culture dishes with feeder layers consisting of mouse embryo fibroblasts. The day after transfection, G418 is added to the media at a concentration of 400 μg/ml and the cells are selected for approximately two weeks. Individual clones are then picked into 24-well plates containing feeder cells and expanded to two 150 mm dishes. Genomic DNA is prepared from one dish and the cells are frozen. DNA from clones is digested with EcoRV, electrophoresed on agarose gels and transferred to nylon membranes for Southern blotting. A 2 Kb EcoRI fragment from the $\beta_2$-M gene (downstream of the homology used for vector construction) is used as a probe (FIG. 3). For the vector, an approximately 17 Kb EcoRV fragment which hybridizes with the probe, is expected when a homologous recombination event has occurred. The non-recombined locus should contain a hybridizing fragment approximately 20 Kb in size. The initial recombinant clones will contain one recombined locus and one non-recombined locus.

In order to obtain recombinant cells that contain the Neo targeting vectors in both copies of the MHC locus (i.e. cells homozygous for the targeting event), cells are selected in higher levels of G418. Alternatively, heterozygous cells may be selected against using a combination of anti-$\beta_2$M or anti-αMHC Class I molecules and complement, or using anti-αMHC Class I antibodies coupled to magnetic beads (Vaccaro, *Am. Biotech. Lab.* 30–35 (1990)). Using vectors that contain a mutant Neo gene concentrations of the selection agent G418 are tested to obtain those that favor the growth of homozygous cells using the procedure described by Mortensen et al., *Molec. and Cell. Biol.* 12(5):2391–2395 (1992). In addition, because non-disjunction is a reciprocal event and the homozygous wild-type cell is very sensitive to G418 selection, low level G418 selection will cause the population of cells to drift towards homozygosity during continuous expansion of the cell population.

In addition to selecting cells that have spontaneously become homozygous, cells homozygous for inactivated $\beta_2$-M genes may be obtained by repeating the homologous targeting using Neo vectors as described above. Using a targeting vector containing the same arms of homology, but having a different mammalian selectable marker, such as hygromycin$^r$ (hyg$^r$), a homozygously targeted clone is produced from a heterozygote at the initial targeting efficiency ($10^{-6}$ to $10^{-7}$, approximately $10^{-2}$ per hyg$^r$ and Neo$^r$ clones).

VII. Targeting of the $\beta_2$-M Locus in Normal Human Keratinocytes

Normal human keratinocytes isolated from human foreskins and grown in the presence of mouse embryo fibroblast feeder cells were transfected using a linearized preparation of the #137 targeting vector described in Example V above. G418$^r$ colonies of the human keratinocytes were selected and screened for expression of the CD4-$\beta_2$M fusion protein as described above. The results from three (3) independent experiments are shown in Table 6.

TABLE 6

Targeting of $\beta_2$M in Human Keratinocytes

| DNA | Positive Clones | Targeting Efficiency |
|---|---|---|
| Not-Cla 148 | 2 | $3.3 \times 10^{-7}$ |
| Not-Cla 148 | 11 | $7.9 \times 10^{-7}$ |
| Not-Cla 137 | 10 | $1.3 \times 10^{-6}$ |

These experiments demonstrated homologous recombination achieved in somatic cells at frequencies very similar to those observed for human RPE cells as described above. The differences observed in the absolute frequencies of targeting is attributable to the differing plating efficiencies of the two cell types, about 90% for the hRPE cells and 5% for the human keratinocytes.

These results demonstrate that homologous recombination can be employed for the directed modification of different human cell types grown in vitro. The results also demonstrate the ability of the targeting constructs and modified ELISA to detect the recombinants generated using these methods. The method of the invention permits the rapid and accurate detection of desired homologous recombination events that may occur at low frequency and be difficult to detect, without harming the viability of the cells being assayed. Thus, it may be applied to intracellular protein targets to permit the production of functional mutant proteins simply by causing the successfully targeted protein to be transported secreted outside the cell for detection.

VIII. Targeting of the IFN-γR Locus in Embryonic Stem Cells

This example describes the targeting of the IFN-γ locus in mouse embryonic stem cells. Because the efficiency of gene targeting in normal somatic cells was expected to be low, methods were developed to enrich for targeting events in mouse embryonic stem (ES) cells which readily undergo homologous recombination.

Construction of targeting plasmids.

A replacement vector, pB-IT1, containing a transcriptionally active neomycin (Neo) selectable marker inserted into an exon of the IFN-γR gene was constructed as follows (FIG. 7). Plasmid pB-I7.2B was used as a source of targeting sequences. This plasmid contains a 7.2 Kb BamHI fragment isolated from a λ phage library prepared from 129 mouse PCC4 cells inserted into plasmid Bluescript (Stratagene, San Diego, Calif.). Oligonucleotides were synthesized based on the published IFN-γR cDNA sequence (Hemmi et al. *Proc. Natl. Acad. Sci. USA* 86:9901–9905 (1989)) and were labeled and used as probes. A 5.2 Kb BamHI-HindIII fragment of pB-I7.2B containing IFN-γR exons IV to VI (FIG. 7B) was then subcloned into pBluescript SK (Stratagene). The resulting plasmid (pB-5.2BH) has within exon VI, which encodes the transmembrane region of the protein, a unique EcoRI site chosen for insertion of the selectable marker gene. Vector pB-IT1 (FIG. 7A) was made by subcloning the entire Neo cassette, a 1.1 Kb XhoI-SalI fragment of pMC1-Neo poly A, into the EcoRI site of pB-5.2BH, using an XhoI-EcoRI adaptor. A subclone with the Neo gene in the same transcriptional orientation as the receptor gene was then selected. After selection for G418 resistance, colonies were screened for homologous recombination. None of the 432 ES cell clones analyzed were targeted, indicating that homologous recombination is a rare event (Table 7). To reduce the number of resistant colonies resulting from illegitimate DNA integration, the promoter-enhancer sequences as well as the translational start (ATG) codon of MC1-Neo in pB-IT1 were deleted by oligonucleotide-directed mutagenesis. The resulting promoterless-Neo vector (pB-IT2) (FIG. 7A) has the second codon (GGA) of the selectable marker fused in frame into the coding region of the receptor gene, downstream from Lys 254 according to Hemmi et al, supra. The IFN-γR sequences in this vector are the same as in pB-IT1. Thus, upon transfection, if homologous recombination between pB-IT2 and the target locus occurs, the Neo gene will be expressed as an IFN-γR-Neo fusion protein. Because the selectable gene was inserted 9 bp downstream from the transmembrane coding region (Hemmi et al., supra), the Neo sequences in the fusion protein should be retained in the cytoplasm conferring resistance to G418. Before electroporation, plasmids were linearized with PvuI which cuts within the Bluescript plasmid.

TABLE 7

| | | Efficiency of Homologous recombination | | | | |
|---|---|---|---|---|---|---|
| Cell Type | Vector | Treated Cells (× 10$^7$) | Total G418$^r$ Anal. | Total IFN-γR$^-$ | IFN-γR$^-$/G418$^r$ (%) | Absol. Targeting Freq. |
| ES CELLS | | | | | | |
| Exp. 1 | pB-IT1 | 6 | 3,480 432* | 0 | 0.0 | 0 |
| Exp. 2 | pB-IT1 | 2 | 3,150 — | — | — | — |
| | pB-IT2 | 14 | 182 124 | 22 | 17.3 | 2.3 × 10$^{-7}$ |
| Exp. 3 | pB-IT2 | 12 | 168 82 | 10 | 12.2 | 1.7 × 10$^{-7}$ |
| MYOBLASTS | | | | | | |
| Exp. 1 | pB-IT2 | 2 | 3,992 200 | 1 | 0.5 | 1.0 × 10$^{-6}$ |
| Exp. 2 | pB-IT2 | 2 | 2,534 200 | 3 | 1.5 | 1.9 × 10$^{-6}$ |

Plating efficiency of electroporated cells ranged from 20–30% in ES cells and from 30–55% in myoblasts. IFN-γR$^-$ are targeted G418$^r$ clones. *Clones were screened by PCR using a 5' primer (5'ACGGTATCGCCGCTCCCGAT3') derived from Neo and a 3' primer (5'GACCTATTTGTGCATTGGAAGC3') derived from IFN-γR genomic sequences external to the targeting vector. 132 of these clones were rescreened by Southern.

Cell culture, electroporation and selection.

To test the enrichment strategy, ES cells were electroporated with vector pI-IT1 or pB-IT2, and selected with G418. The ES cell line E14TG2a (Hooper et al. *Nature* 326:292–295 (1987), provided by Dr. Oliver Smithies, University of North Carolina, Chapel Hill, N.C.) was cultured on mitotically inactive STO fibroblasts resistant to G418 (NSTO) as described by Robertson, in *Teratocarcinomas and Embryonic Stem Cells: a Practical Approach*, ed. Robertson (IRL Oxford), pp. 71–112 (1987). To culture the ES cell line El4–1 (Kuhn et al. *Science* 254:707–710 (1991)) embryonic primary fibroblasts were used as a feeder layer and recombinant murine leukemia inhibitory factor (10$^4$ U/ml) was added to the media.

In addition, the ability of mouse myoblasts to carry out homologous recombination was investigated using the above-described strategy for highly efficient homologous recombination to inactivate IFN-γR gene in mouse ES cells. Myoblasts were isolated from the skeletal muscle of 14 day old mice (C57BL/6×129) using 0.5% collagenase, preplated for 2 hours to reduce fibroblast contamination and then seeded at 10$^5$ cells/cm$^2$ in F10 supplemented media (fresh media with 10% fetal calf serum, 5% horse serum, 2 mM glutamine, 0.5% chick embryo extract, 20 ng/ml basic fibroblast growth factor and conditioned media from mouse muscle fibroblasts, 1:1). Cells with myoblast morphology were cloned and cultured in F-10 supplemented medium with fibroblast conditioned medium for up to 100 doublings. Under these culture conditions, cells express the same phenotype and growth regulation as primary isolated myoblasts and maintain their ability to differentiate and form contracting myotubes (Austin et al., *In vitro* 29A:105A (1993)). Clones were picked and expanded. Very little clonal variation in growth and morphology was observed.

ES cells (2×10$^7$) or myoblasts (1×10$^7$) were electroporated in 0.8 ml of Ca$^{2+}$ and Mg$^{2+}$ free phosphate-buffered media (ES cells) or 0.5 ml F10 media (myoblasts) with 10 μg of linearized plasmid DNA at 600 V/cm and 500 μF (ES cells) or at 875 V/cm and 960 μF (myoblasts) in a Bio-Rad gene pulser. Electroporated cells were plated and medium replaced after 24 hours (ES cells) or 48 hours (myoblasts) with medium containing 100 μg/ml G418 (active form). Individual G418-resistant colonies were picked after 10–18 days (ES cells) and 10–12 day myoblasts and allowed to expand.

ES cells electroporated with pB-IT2 formed G418-resistant colonies demonstrating that the selectable gene in the IFN-γR-Neo construct was functional. The number of colonies obtained with the transcriptionally silent targeting vector pB-IT2, was considerably lower (120-fold) than the number obtained with the full-function targeting vector (Table 7).

Myoblasts electroporated with vector pB-IT2 also formed G418-resistant colonies. The frequency of G418-resistant colonies per total electroporated cells was 120-fold greater for myoblasts than ES cells (Table 7).

Screening.

Figure 8A:
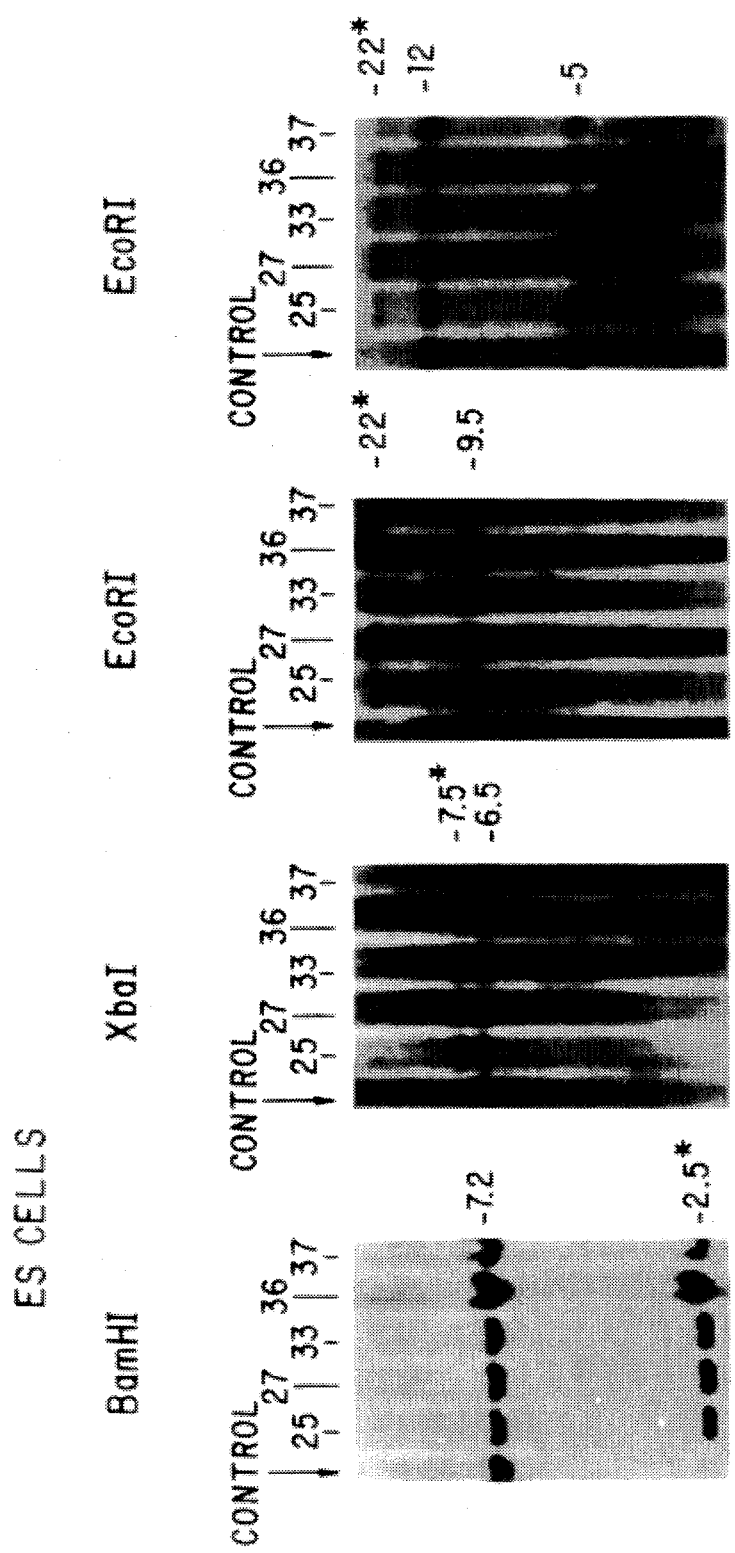
FIG. 8 A–B are photographs from Southern analysis of the IFNγR locus in ES cells (FIG. 8A) and myoblasts (FIG. 8B), as described in Example VIII, infra (molecular sizes of restriction fragments in kilobases are shown; *=mutant allele).
Figure 8B:
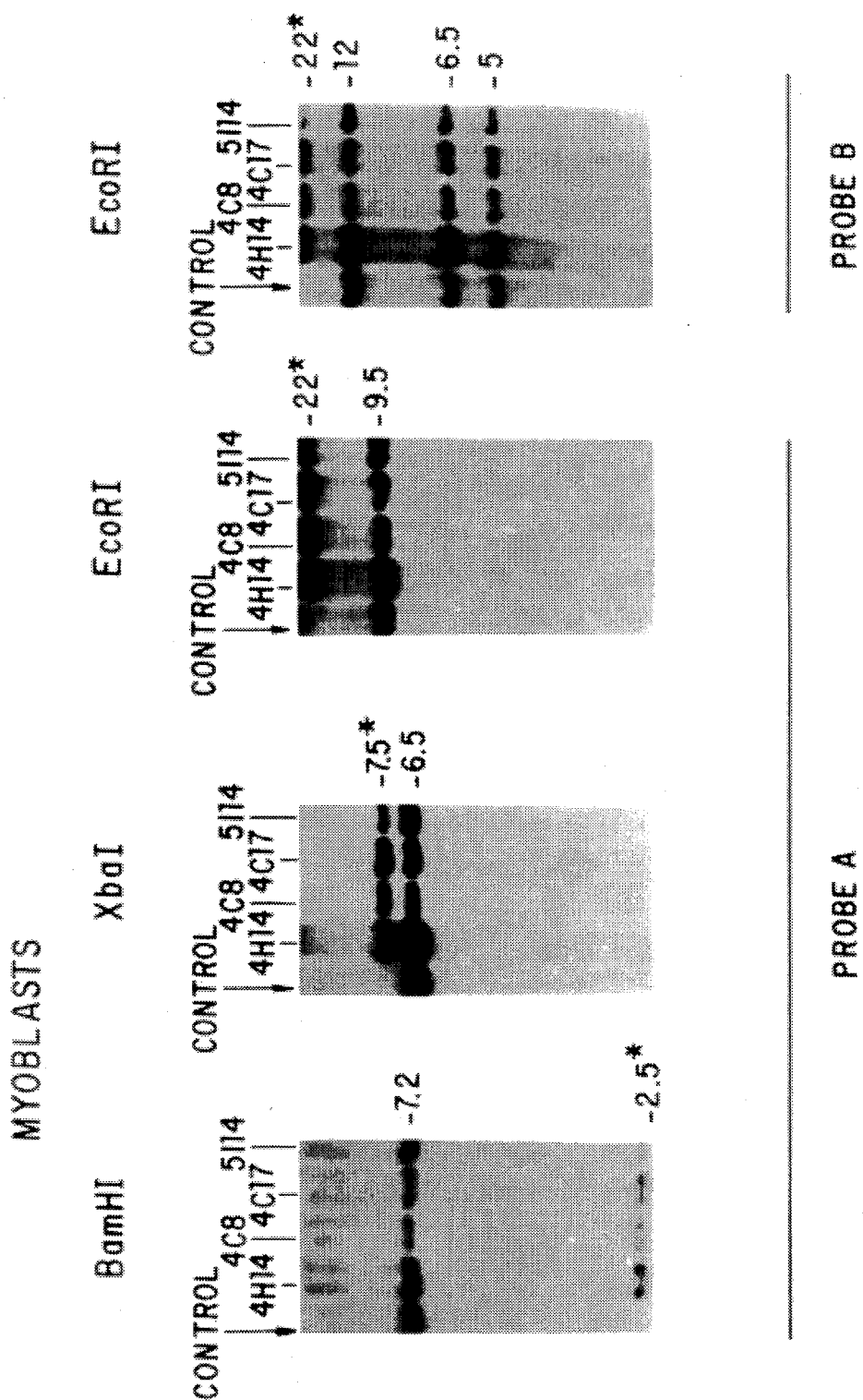
Figure 9A:
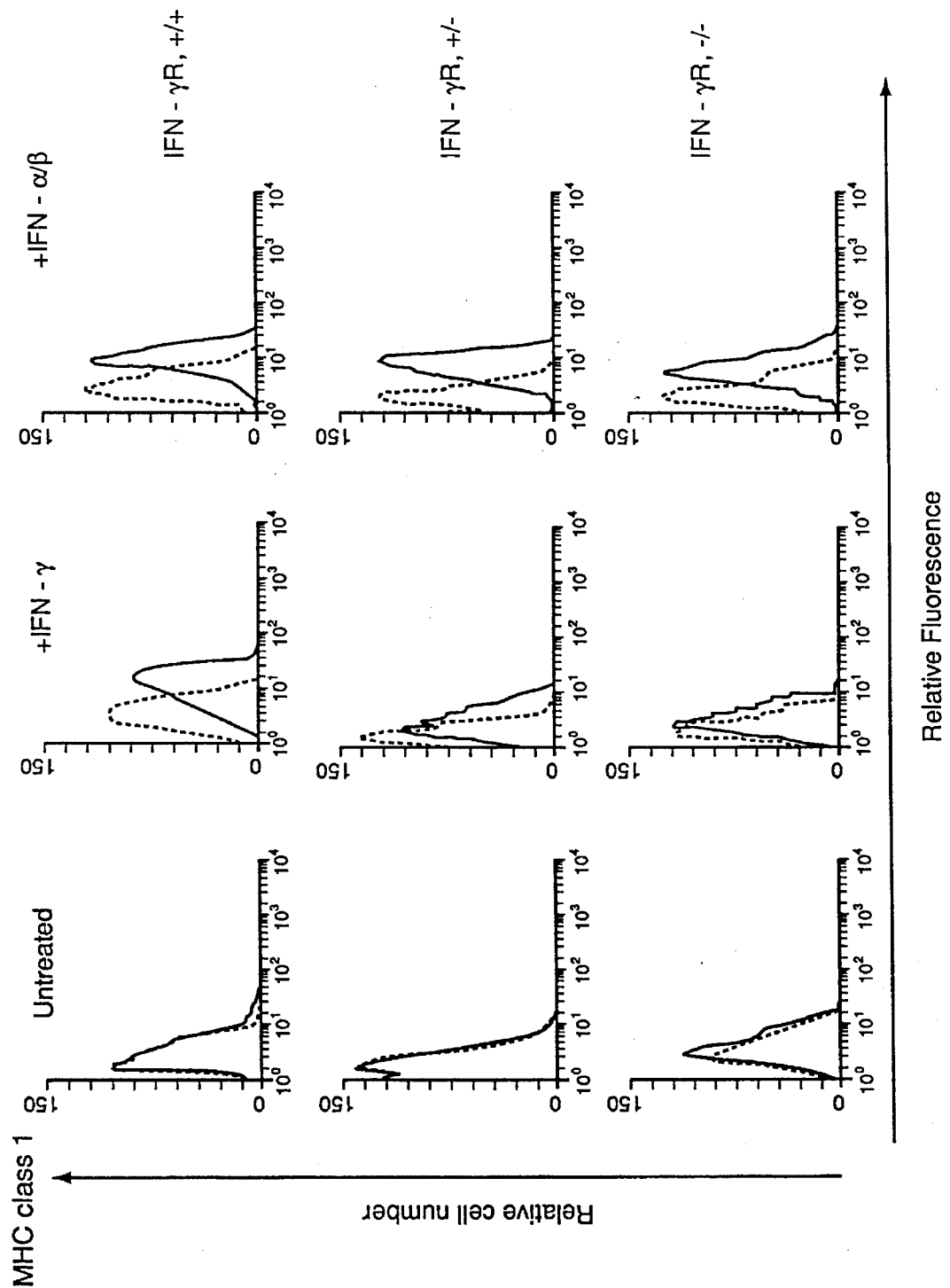
FIG. 9A shows expression of MHC Class I antigens and the IFNγR binding domain in the parental myoblast cell line (IFNγR, +/+), the targeted myoblast cell line 4C17 (IFNγR, +/–) and myoblasts isolated from homozygous mutant mice (IFNγR, –/–)

Resistant ES cell colonies generated with vector pB-IT2 were screened for homologous recombination as follows. BamHI-digested genomic DNA (6 to 10 μg) was separated by electrophoresis through a 0.8% agarose gel, transferred to nylon membranes (Zeta bind, Cuno Laboratory Products, Meriden, Conn.) and hybridized, under standard conditions, with a IFN-γR probe (probe A) lying 3' of the targeting vector sequences (FIG. 8C). Insertion of the Neo gene into the target locus should give, in addition to a 7.2 Kb wild-type BamHI fragment, a new 2.5 Kb BamHI fragment that hybridizes with this probe. From a total of 206 G418-resistant colonies generated in two different experiments, 32 showed the 2.5 Kb BamHI fragment predicted for a targeted locus (Table 7). DNA from five of the recombinant clones positive by this method were further expanded and analyzed. Genomic DNA was digested with EcoRI or XbaI and hybridized either with probe A or with a 5' IFN-γR external probe (B) also external to the targeting vector (FIG. 8C). Probes were generated by the polymerase chain reaction (PCR) using as DNA template a cDNA clone (probe B) or pB-I7.2B (probe A). These probes correspond to nucleotides 103 to 486 (probe B) and 1000 to 1666 (probe A) (Hemmi et al., supra). The IFN-γR cDNA was generated by reverse transcription of total RNA isolated from mouse EL-4 cells and amplification of the product by PCR. Because the EcoRI site in exon VI is removed in the targeting vector, EcoRI-digested DNA from a correctly targeted clone gave a fragment of 22.5 Kb that hybridized with both probes. This new EcoRI fragment consists of the region covered by the 9.5 Kb EcoRI fragment hybridizing with probe A, the 12 Kb EcoRI fragment hybridizing with probe B and the inserted Neo gene. As shown in FIG. 9A a new fragment of approximately 22 Kb was detected in all five clones, indicating homologous recombination between the vector and the target locus. In accordance, DNA from the same clones digested with XbaI and hybridized with probe A gave a new 7.5 Kb fragment, resulting from the insertion of Neo into the endogenous 6.5 Kb XbaI fragment. The frequency of recombination events (⅙) obtained with vector pB-IT2 demonstrated that the absence of sequences in the targeting vector necessary for transcription and translation of the selectable marker increased the relative gene targeting frequency at least 70-fold.

Figure 9B:
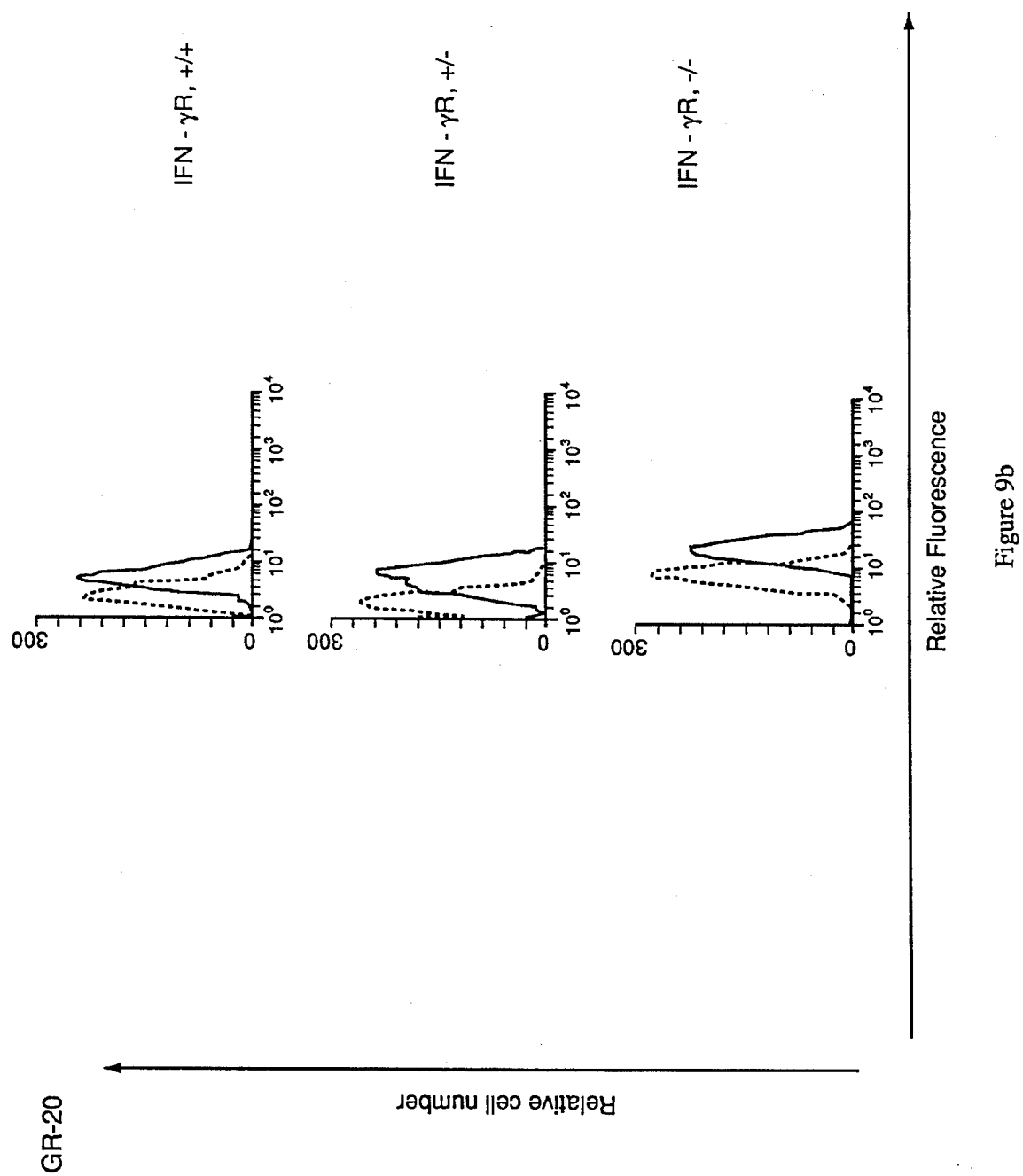
FIG. 9B shows GR-20 antigen expression in mouse myoblasts (dotted lines represent background binding of the fluorescent antibody).

A total of 400 G418-resistant myoblast colonies were picked, expanded and screened by Southern blot analysis. Four of these clones were found to be correctly targeted at the IFN-γR locus (FIG. 9B). The frequency of homologous recombinants was found to be approximately ¹/₁₀₀ of G418-resistant myoblasts. While the relative frequency of gene targeting in myoblasts was lower than that observed for ES cells (⅙) homologous recombinants per total G418 resistant colonies was approximately 15-fold greater in ES cells than myoblasts, the absolute gene targeting frequency in myoblasts was found to be approximately 8-fold greater ($1.6 \times 10^{-6}$ for myoblasts and $2.1 \times 10^{-7}$ for ES cells) (Table 7).

IX. Expression of MHC Antigens in IFN-γR Targeted Myoblasts

The IFN-γR-Neo hybrid protein generated by homologous recombination as described above, contains the extracellular and transmembrane domains of the native receptor, but not the cytoplasmic domain, which has been demonstrated to be essential for cellular signal transduction after IFN-γ treatment (Farrar et al., *J. Biol. Chem.* 266:19626–19635 (1991)). To determine whether this mutation is capable of abolishing IFN-γR function, the induction of MHC Class I antigen expression, mediated by the IFN-γR was evaluated in myoblasts carrying one or two copies of the disrupted IFN-γR allele. Myoblasts bearing two copies of the mutation were isolated from the muscle of transgenic mice homozygous for the mutation. Transgenic mice were generated by injecting an E14-1 ES cell line carrying a correct disrupted IFN-γR allele into blastocysts as follows.

Generation of chimeric mice.

Blastocyst manipulations were performed as described by Koller et al., *Proc. Natl. Acad. Sci. USA* 86:8932–8935 (1989)). Briefly, modified ES cells were injected into blastocysts obtained from superovulated C57BL/6 females and reimplanted into the uteri of a pseudopregnant recipient. Chimeric mice, according to coat color, were mated to C57BL/6 mice, and homozygous mutant animals were obtained by breeding heterozygous offspring. Transmission of the modified IFN-γR allele in the Agouti offspring was tested by Southern blotting of DNA obtained from tail biopsies.

Cytofluorometric analysis.

To induce MHC Class I antigen expression, the parental myoblast cell line (IFNγR, +/+), in vitro targeted myoblast cell line 4C17 (IFN-γR, +/−) and myoblasts isolated from IFN-γR homozygous mutant mice (−/−) were cultured for 24 hours with culture medium alone (untreated cells) or in the presence or absence of IFN-γ (1,000 U/ml), or a mixture of mouse IFN-α and β (1200 U/ml, 1:9). Expression of MHC Class I antigens was determined using specific immunofluorescence staining. Myoblasts were removed from culture dishes with 0.05% EDTA solution washed and incubated ($10^6$ cells) for 30 minutes with 28-14-8S (ATCC, Rockville, Md.) monoclonal anti-H-2D$^b$ antibody. After two washes, cells were incubated for another 30 minutes with a FITC-conjugated goat anti-mouse IgG2a antibody (Boehringer Mannheim, Indianapolis, Ind.). To determine whether or not the IFN-γR-Neo hybrid protein was expressed on the cell surface, cells were stained with GR20, a rat monoclonal antibody that recognizes the binding site for IFN-γ (Basu et al., *J. Interferon. Res.* 9:551–562 (1989)) and goat anti-rat IgG-FITC (Caltag Laboratories, S. San Francisco, Calif.). Cells were washed and cellular fluorescence measured with a Becton Dickinson FACScan flow cytometer.

Class I antigens in untreated myoblasts were undetectable in all three cell types. IFN-γ induced Class I expression in (+/+) and (+/−) myoblasts but not in (−/−) myoblasts (FIG. 10A). The response induced in (+/−) myoblasts was 38–60% less than in (+/+) myoblasts, indicating that disruption of one IFN-γR allele causes a reduction of IFN-γR function. In contrast, the expression of Class I induced by a mixture of IFN-α and γ, which bind to different receptor, was similar for all three cell types (FIG. 10A). Myoblasts from IFN-γ (−/−) mice expressed GR-20 epitopes at levels that were comparable to those found in wild type (+/+) and 4C17 (+/−) myoblasts (FIG. 10B). Thus, myoblasts which are homozygous or heterozygous for the inactivated IFN-γ gene have a significantly diminished response to IFN-γ despite the expression of an IFN-γ extracellular domain on their cell surface.

Characterization of gene targeted myoblasts

Targeted myoblast clones were characterized to determine whether they retained the properties of normal parental myoblasts. Targeted clones 4H14, 4C8, 4C17 and 5114 (FIG. 9B) were characterized by chromosomal analysis and anchorage independent growth assays as described below. No differences in morphology or culture requirements were observed between these cells and primary myoblasts (i.e. cells taken directly from the animal and cultured, but never passaged). Under conditions that prevent myoblast differentiation, the targeted myoblasts were small and refractile and displayed the same rounded shape and basal pseudopodia as primary myoblasts (FIG. 10A). The targeted cells retained their ability to differentiate and form contracting myotubes when cultured in differentiation medium (5% horse serum in DMEM). The cells initially elongate, display a bipolar morphology and fuse to form multinucleated myotubes (FIG. 10B).

To ensure that the myoblasts had not been transformed, a chromosomal analysis was carried out, and the capacity of the targeted cells to form tumors in nude mice and to grow in soft agar was studied. Chromosome analysis was performed by preparing metaphase spreads from each targeted clone as follows:

Chromosome analysis.

Metaphase spreads of myoblasts were made by first treating cells in logarithmic growth phase with 0.4 μg/ml demacolcine for 7 hours. Cells were then harvested and treated with 0.075M KCl for 10 minutes, fixed with 3:1 MeOH/HAc three times for 10 minutes, and dropped onto cold, wet, precleaned slides (Worton et al. *Methods Enzymol.* 58:322–344 (1979)). G-banding was performed on aged slides using 0.1% Trypsin for 20–30 seconds followed by 4% Giemsa (Harleco) staining in Gurr's buffer (pH 6.8) (Verma & Babu, in Human chromosomes: Manual of basic techniques (Pergamon Press, N.Y.) pp. 45–113 (1989)). One hundred well-defined metaphase spreads were analyzed for chromosome modality. G-banded spreads were photographed with Kodak Technical Pan film, printed and analyzed.

Figure 10C:
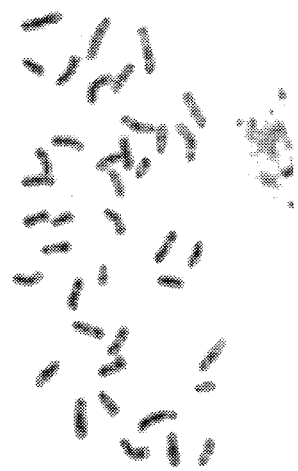
FIG. 10C shows a G-banded metaphase spread.
Figure 10B:
FIG. 10B shows differentiating targeted myoblasts when media is switched to 5% horse serum in DMEM (arrow=multinucleated myotubes)
Figure 10A:
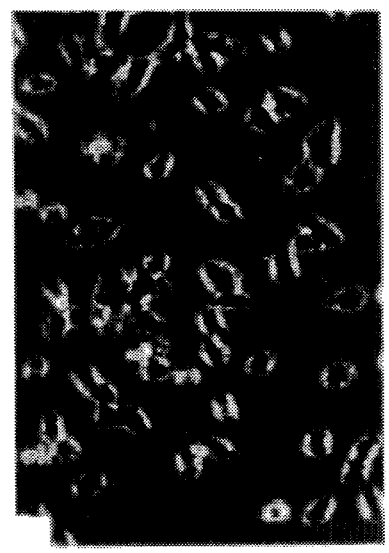
FIG. 10A shows the morphology of freshly isolated myoblasts in G418 resistant colonies.

A modal chromosome number of 40 (2n=40) was observed in all clones with three of the four greater than 79% (FIG. 10C). G-banded chromosomes from 19 metaphase spreads of myoblast cell line 4C17 (+/−) were arranged in karyotypes, ordered and analyzed according to Nesbitt and Francke, *Chromosoma (Berl.)* 41:145–158 (1973). All spreads showed a stable chromosome number with all pairs represented. No apparent structural chromosome abnormalities were observed.

For further characterization, anchorage independent cell growth of the targeted myoblast clones was tested as follows:

Anchorage independent growth.

7 ml of 0.5% agar in 15% serum containing medium was placed in 6 cm dishes and overlayed with $10^4$ cells suspended in 1.5 ml of 0.3% soft agar medium. Cultures were incubated at 37° C. for 15 days at which time they were analyzed for colony growth (Macpherson et al., *Virology* 23:291–294 (1964)). A positive colony was scored if it possessed a diameter greater than 0.1 mm. The transformed control line NMU2 grew and formed colonies in soft agar, whereas no colonies were formed by any of the four targeted myoblast clones (Table 8).

TABLE 8

Anchorage Independent Growth and Tumorigenicity

| Myoblasts | Soft Agar | Tumor Formation | |
|---|---|---|---|
| IFN-γR (+/−) | No. Colonies | Sites | Tumors |
| Control | 2160 | 8 | 8 |
| 4H14 | None | 4 | None |
| 4C8 | None | 4 | None |
| 4C17 | None | 4 | None |
| 5I14 | None | 4 | None |

Control cells are a transformed myoblast cell line (NMU2) derived from the $C_2C_{12}$ parent myoblast cell line. Clones 4H14, 4C8, 4C17 and 5I14 are IFN-γR targeted myoblast clones.

Additionally, tumor forming ability was measured as follows:

Tumorigenicity.

$10^6$ cells were suspended in 50 μl PBS and injected subcutaneously at two sites into 4–6 week old nude mice (CD-1BR, Charles River Lab, Wilmington, Mass.). As a positive control, normal myoblasts were compared with the transformed myoblast mutant (NMU2, Rastinejad et al., *Cell* 72:903–917 (1993)). Animals were analyzed for tumor formation between 7 and 10 weeks.

None of the four targeted myoblast clones formed tumors. In contrast, the NMU2 control cells readily formed tumors (Table 8). These results strongly suggest that the targeted myoblasts were not transformed during selection and subsequent culture.

Thus, as indicated by the morphology, cell growth and ability to differentiate and form myotubes, the targeted clones exhibit the normal properties of primary myoblasts. No indications of cell transformations or abnormal karyotype were observed for the targeted mouse myoblasts. Restriction mapping of the IFN-γR locus HERE targeted in myoblasts did not reveal any unpredicted DNA rearrangements. These results demonstrate that normal mammalian somatic cells, such as myoblasts, genetically modified by gene targeting using the methods of the invention, maintain the properties of primary cells and may be useful for gene therapy in humans.

The method exemplified herein used to target genes in myoblasts provides significant enrichment for homologous recombination events, which might otherwise be difficult to detect in these normal somatic cells because of the expected lower frequency of occurrence. Use of a novel targeting vector employing a transcriptionally and translationally impaired selectable gene such as Neo inserted into the coding region of the target gene, IFN-γR, encoding an integral membrane protein, resulted in the production of a hybrid protein having the selectable marker fused to the transmembrane domain of the target gene, so that the selectable marker is expressed on the cytoplasmic side of the membrane. This targeting vector permitted substantial enrichment for recombinant events in ES cells and myoblasts, suggesting that a membrane-bound Neo polypeptide is efficient in conferring drug resistance. The above experiments produced an increase in the relative gene targeting frequency in ES cells of at least 70-fold.

In accordance with the above results, cells can be provided which should not be subject to immune destruction as a result of the presence of functional Class I MHC antigens. The cells may find wide use, since they will not be subject to immune attack when introduced into an allogeneic host, while they will still be capable of functioning in their native manner. In this way, a wide range of diseases resulting from the loss of number and/or function of cells may be treated, where the introduced cells will survive, multiply and function. Therefore, not only may diseases as a result of burns, abrasions, pathogens or the like be treated, but also diseases as a result of genetic defects.

Also, embryonic stem cells may be modified by homologous recombination to provide for chimeric mammalian hosts. The chimeric mammalian hosts may then be selected and used for breeding to produce homozygous hosts lacking the inactivated gene and may then be used as a source of tissues and cells for transplantation, as a model for transplantation therapies, and experimentally to test for drug efficacy.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of producing a genetically engineered mouse lacking functional Class I and II major histocompatibility complex (MHC) antigens, said method comprising:

(a) transfecting embryonic stem cells from a mouse with a DNA construct comprising a selectable marker gene and at least 100 bp of DNA sequence homologous with a sequence of the endogenous IFNγR present in a chromosome of said embryonic stem cells under conditions where said construct becomes integrated into said chromosome by homologous recombination, thereby inactivating said IFNγR gene;

(b) selecting and screening for mouse embryonic stem cells which carry said inactivated IFNγR gene to provide selected cells;

(c) introducing said selected cells into the blastocyst of a developing mouse embryo;

(d) allowing said embryo to develop to term;

(e) identifying at least one offspring which carries said inactivated IFNγR gene in the germ line; and (f) breeding said offspring to produce a homozygous mouse lacking functional Class I and II MHC antigens.

2. A method according to claim 1, wherein said selectable marker gene is an antibiotic resistance gene and said step of selecting is by means of an antibiotic.

3. A method according to claim 2, wherein said selectable marker gene is the neomycin resistance gene and said antibiotic is G418.

4. A genetically engineered mouse produced by the method according to claim 1.

5. A genetically engineered mouse characterized by lacking functional class I and II major histocompatibility complex antigens as a result of introduction of a DNA construct into embryonic stem cell producing a lesion that results in inactivation of the IFNγR gene.

6. A method for determining the effectiveness of a therapeutic agent in preventing transplant rejection in a mouse, the method comprising:

(a) administering said therapeutic agent to said mouse, said move being characterized by lacking functional Class I and II MHC antigens resulting from inactivation of the IFNγR gene, and having transplanted genetically engineered tissue or cells; and (b) determining the presence or absence of rejection of said transplanted tissue or cells over time in response to said therapeutic agent.

7. A method according to claim 6, wherein said therapeutic agent is an immunosuppressive agent.

8. A method according to claim 7, wherein said immunosuppressive agent is cyclosporine.

* * * * *